(12) United States Patent
Sakugawa et al.

(10) Patent No.: US 11,045,796 B2
(45) Date of Patent: Jun. 29, 2021

(54) PROCESS FOR PRODUCING AROMATIC COMPOUND, AND PALLADIUM COMPLEX

(71) Applicant: Sumitomo Chemical Company, Limited, Tokyo (JP)

(72) Inventors: Nanase Sakugawa, Osaka (JP); Takashi Kamikawa, Osaka (JP)

(73) Assignee: SUMITOMO CHEMICAL COMPANY, LIMITED, Tokyo (JP)

(*) Notice: Subject to any disclaimer, the term of this patent is extended or adjusted under 35 U.S.C. 154(b) by 249 days.

(21) Appl. No.: 15/780,352

(22) PCT Filed: Nov. 28, 2016

(86) PCT No.: PCT/JP2016/085156
§ 371 (c)(1),
(2) Date: May 31, 2018

(87) PCT Pub. No.: WO2017/094655
PCT Pub. Date: Jun. 8, 2017

(65) Prior Publication Data
US 2018/0369799 A1    Dec. 27, 2018

(30) Foreign Application Priority Data
Dec. 2, 2015    (JP) .............................. JP2015-235404

(51) Int. Cl.
| | |
|---|---|
| *B01J 31/00* | (2006.01) |
| *B01J 31/24* | (2006.01) |
| *C07C 15/14* | (2006.01) |
| *B01J 31/22* | (2006.01) |
| *C07F 15/00* | (2006.01) |
| *C08G 61/12* | (2006.01) |

(Continued)

(52) U.S. Cl.
CPC ........... *B01J 31/2404* (2013.01); *B01J 31/22* (2013.01); *B01J 31/24* (2013.01); *C07C 1/32* (2013.01); *C07C 15/14* (2013.01); *C07D 333/08* (2013.01); *C07F 15/00* (2013.01); *C08G 61/12* (2013.01); *B01J 2231/4216* (2013.01); *B01J 2231/4227* (2013.01); *B01J 2531/0205* (2013.01); *B01J 2531/824* (2013.01); *C07B 61/00* (2013.01)

(58) Field of Classification Search
CPC .................................................... B01J 31/2404
USPC ........................................................ 502/155
See application file for complete search history.

(56) References Cited

U.S. PATENT DOCUMENTS

| | | |
|---|---|---|
| 6,034,240 A | 3/2000 | La Pointe |
| 6,043,363 A | 3/2000 | LaPointe et al. |

(Continued)

FOREIGN PATENT DOCUMENTS

| | | |
|---|---|---|
| EP | 2492274 A1 | 8/2012 |
| EP | 2871199 A1 | 5/2015 |

(Continued)

OTHER PUBLICATIONS

Jang S Kim: "Synthesis and reactivity of bimetallic palladium(ii) methyl complexes with new functional phosphine ligands", Journal of the Chemical Society, Dalton Transactions, No. 24, Nov. 7, 2002 (Nov. 7, 2002), p. 4 726-4 731 (Year: 2002).*

(Continued)

*Primary Examiner* — Stefanie J Cohen
(74) *Attorney, Agent, or Firm* — Panitch Schwarze Belisario & Nadel LLP

(57) ABSTRACT

A process for producing an aromatic compound in high yield and a palladium complex are provided. The palladium complex is represented by formula (D) or formula (D'):

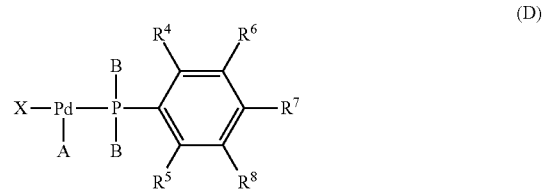

In formula (D), X represents a chlorine atom, A represents an alkyl group having 1 to 3 carbon atoms, B represents an alkyl group having 4 to 20 carbon atoms or a cycloalkyl group having 5 to 10 carbon atoms, $R^4$ and $R^5$ each independently represent a hydrogen atom, a fluorine atom, or an alkoxy group having 1 to 20 carbon atoms, and $R^6$, $R^7$ and $R^8$ represent a hydrogen atom, an alkyl group having 1 to 20 carbon atoms, an aryl group having 6 to 20 carbon atoms or a heteroaryl group having 4 to 20 carbon atoms.

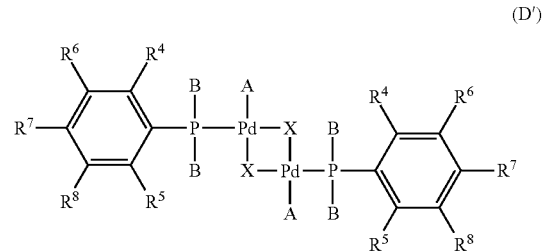

In formula (D'), X, A, B and $R^4$ to $R^8$ are the same as defined above.

5 Claims, No Drawings

(51) Int. Cl.
*C07C 1/32* (2006.01)
*C07D 333/08* (2006.01)
*C07B 61/00* (2006.01)

(56) References Cited

U.S. PATENT DOCUMENTS

| | | | |
|---|---|---|---|
| 6,177,528 B1 | 1/2001 | LaPointe et al. | |
| 2011/0187266 A1* | 8/2011 | Fukushima | H01L 51/0039 |
| | | | 313/504 |
| 2012/0197030 A1* | 8/2012 | Ma | C07B 37/04 |
| | | | 549/295 |
| 2013/0165660 A1* | 6/2013 | Colacot | B01J 31/2295 |
| | | | 546/346 |
| 2015/0322101 A1 | 11/2015 | Oda et al. | |
| 2015/0322199 A1 | 11/2015 | Oda et al. | |

FOREIGN PATENT DOCUMENTS

| | | |
|---|---|---|
| JP | H03261793 A | 11/1991 |
| JP | 2013189602 A | 9/2013 |
| JP | 2014162745 A | 9/2014 |
| WO | 9946271 A1 | 9/1999 |
| WO | 0116057 A1 | 3/2001 |
| WO | 2006093213 A1 | 9/2006 |
| WO | 2011161451 A1 | 12/2011 |
| WO | 2014007404 A1 | 1/2014 |
| WO | 2014007405 A1 | 1/2014 |

OTHER PUBLICATIONS

Office Action dated Jun. 19, 2020 in CN Application No. 201680070060.8 (English Machine Translation Only).
Office Action dated Jun. 22, 2020 in in Application No. 201847023944.
English Translation of Office Action dated Feb. 7, 2020 in TW Application No. 105139214.
English Translation of Office Action dated Dec. 18, 2019 in CN Application No. 201680070060.8.
Extended European Search Report dated Dec. 19, 2019 in EP Application No. 16870592.9.
Mahamo et al., "Neutral palladium(II) complexes with P,N Schiff-base ligands: Synthesis, characterization and application as Suzuki-Miyaura coupling catalysts," Journal of Organo-Metallic Chemistry, vol. 703, pp. 34-42 (2012).
Office Action dated Mar. 19, 2020 in JP Application No. 2017553834 (English Machine Translation only).
Int'l Preliminary Report on Patentability dated Jun. 14, 2018 in Int'l Application No. PCT/JP2016/085156.
Int'l Search Report dated Feb. 21, 2017 in Int'l Application No. PCT/JP2016/085156.
Kim et al., "Synthesis and reactivity of bimetallic palladium(II) methyl complexes with new functional phosphine ligands," Journal of the Chemical Society, Dalton Transactions, pp. 4726-4731 (2002).
Miyaura et al., "The Palladium-Catalyzed Cross-Coupling Reaction of Phenylboronic Acid With Haloarenes in the Presence of Bases," Synthetic Communications: An International Journal for Rapid Communication of Synthetic Organic Chemistry, vol. 11, No. 7, pp. 513-519 (1981).

* cited by examiner

PROCESS FOR PRODUCING AROMATIC COMPOUND, AND PALLADIUM COMPLEX

CROSS-REFERENCE TO RELATED APPLICATIONS

This application is a Section 371 of International Application No. PCT/JP2016/085156, filed Nov. 28, 2016, which was published in the Japanese language on Jun. 8, 2017 under International Publication No. WO 2017/094655 A1, which claims priority under 35 U.S.C. § 119(b) to Japanese Application No. 2015-235404, filed Dec. 2, 2015, the disclosures of which are incorporated herein by reference in their entirety.

TECHNICAL FIELD

The present invention provided relates to a process for producing an aromatic compound and a palladium complex.

BACKGROUND ART

Aromatic compounds having a structure in which two or more aromatic rings are n-conjugated are useful, for example, for medicinal products and organic electronics materials, and in the field of the organic electronics material, there are many reports on, in particular, aromatic compounds having a hetero ring. As a general process for producing an aromatic compound, a process utilizing the Suzuki coupling has been known (Non-Patent document 1).

PRIOR ART DOCUMENT

Patent Document
Non-Patent document 1: Synthetic Communications, 11(7), 513, 1981.

SUMMARY OF THE INVENTION

Problem to be Solved by the Invention

In the process for producing an aromatic compound described in Non-Patent document 1, however, boronic acid is decomposed and a yield of an aromatic compound is not necessarily sufficient. Then, the present invention has an object of providing a process for producing an aromatic compound with high yield, and a catalyst used in the process.

Means for Solving the Problem

Under such circumstances, the present inventors have intensively studied a process for producing an aromatic compound using a palladium complex as a catalyst for the Suzuki coupling, leading resultantly to the following present inventions ([1] to [15]).

[1] A palladium complex represented by the formula (D):

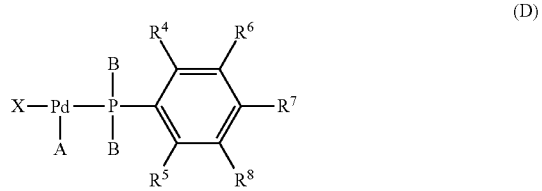

wherein,

X represents a chlorine atom, a bromine atom or an iodine atom,

A represents an alkyl group having a number of carbon atoms of 1 to 3,

B represents an alkyl group having a number of carbon atoms of 4 to 20 or a cycloalkyl group having a number of carbon atoms of 5 to 10, $R^4$ and $R^5$ each independently represent a hydrogen atom, a fluorine atom, an alkoxy group having a number of carbon atoms of 1 to 20 or a cycloalkoxy group having a number of carbon atoms of 5 to 10, $R^6$, $R^7$ and $R^8$ each independently represent a hydrogen atom, a fluorine atom, an alkyl group having a number of carbon atoms of 1 to 20, a cycloalkyl group having a number of carbon atoms of 5 to 10, an aryl group having a number of carbon atoms of 6 to 20 and optionally having a substituent or a heteroaryl group having a number of carbon atoms of 4 to 20 and optionally having a substituent, the number of carbon atoms of the aryl group and the heteroaryl group does not include the number of carbon atoms of the substituent, the substituent which the aryl group and the heteroaryl group optionally have is selected from the following Group 1, and all of $R^4$ to $R^8$ does not represent a hydrogen atom at the same time, or the formula (D'):

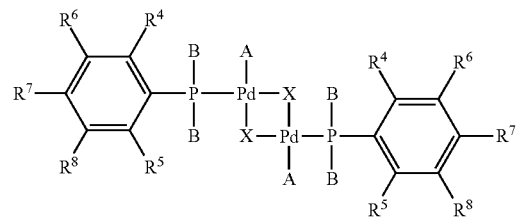

wherein,

X, A, B and $R^4$ to $R^8$ are the same as defined above, the plurality of X, A, B and $R^4$ to $R^8$ may be the same or different at each occurrence;

Group 1: a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocycle group optionally having an alkyl group, a group represented by —N(R')$_2$ wherein two R' each independently represent a hydrogen atom, a hydrocarbon group having a number of carbon atoms of 1 to 20 or a heterocycle group optionally having an alkyl group, a group represented by —Si(R')$_3$ wherein R' is the same as defined above and three R' may be the same or different at each occurrence, an acyl group, a group having a carbon atom-nitrogen atom double bond, an acid imide group, an alkoxycarbonyl group, a cycloalkoxycarbonyl group, an aryloxycarbonyl group, a carboxy group, a cyano group, a nitrile group and a nitro group.

[2] The palladium complex according to [1], wherein A is a methyl group.

[3] The palladium complex according to [1] or [2], wherein B is an alkyl group having a number of carbon atoms of 4 to 20.

[4] The palladium complex according to [3], wherein B is an alkyl group having a number of carbon atoms of 4 to 6.

[5] The palladium complex according to [4], wherein B is a tert-butyl group.

[6] The palladium complex according to any one of [1] to [5], wherein $R^4$ and $R^5$ are each a hydrogen atom.

[7] A process for producing an aromatic compound comprising a step of reacting a compound represented by the formula (A):

$$Ar^1\text{-(}X^1\text{)}_m \quad (A)$$

wherein, $X^1$ represents a group represented by any one of the formula (1) to the formula (12), M represents a group I element, and when a plurality of $X^1$ are present, the plurality of $X^1$ may be the same or different,

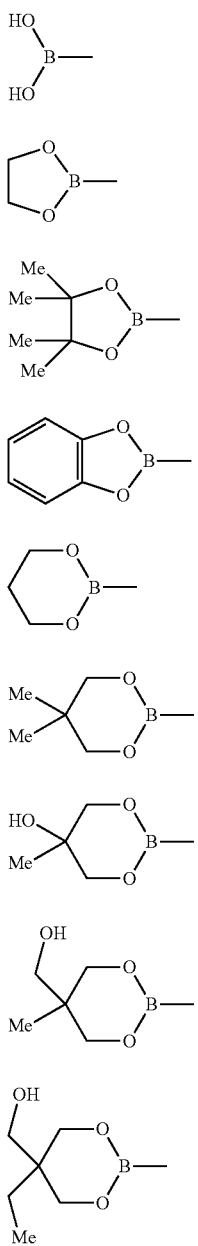

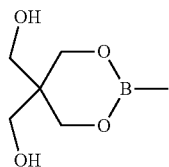

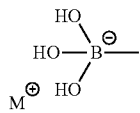

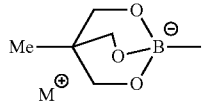

m represents 1 or 2, $Ar^1$ represents an aryl group having a number of carbon atoms of 6 to 36 and optionally having a substituent or a heteroaryl group having a number of carbon atoms of 4 to 36 and optionally having a substituent when m is 1, $Ar^1$ represents an arylene group having a number of carbon atoms of 6 to 36 and optionally having a substituent or a heteroarylene group having a number of carbon atoms of 4 to 36 and optionally having a substituent when m is 2, the number of carbon atoms of these groups does not include the number of carbon atoms of the substituent, the substituent which these groups optionally have is selected from Group 1, the aryl group may be a monovalent group formed by directly linking two or more monocyclic and/or condensed-cyclic aryl groups at each occurrence or by indirectly two or more monocyclic and/or condensed-cyclic aryl groups via a hetero atom or a carbonyl group at each occurrence, the heteroaryl group may be a monovalent group formed by directly linking two or more monocyclic and/or condensed-cyclic heteroaryl groups at each occurrence or by indirectly linking two or more monocyclic and/or condensed-cyclic heteroaryl groups via a hetero atom or a carbonyl group at each occurrence, or may be a monovalent group formed by directly linking at least one monocyclic and/or condensed-cyclic heteroaryl group to at least one monocyclic and/or condensed-cyclic aryl group at each occurrence or by indirectly linking at least one monocyclic and/or condensed-cyclic heteroaryl group to at least one monocyclic and/or condensed-cyclic aryl group via a hetero atom or a carbonyl group at each occurrence, the arylene group may be a divalent group formed by directly linking two or more monocyclic and/or condensed-cyclic arylene groups at each occurrence or by indirectly two or more monocyclic and/or condensed-cyclic arylene groups via a hetero atom or a carbonyl group at each occurrence, and the heteroarylene group may be a divalent group formed by directly linking two or more monocyclic and/or condensed-cyclic heteroarylene groups at each occurrence or by indirectly linking two or more monocyclic and/or condensed-cyclic heteroarylene groups via a hetero atom or a carbonyl group at each occurrence, or may be a divalent group formed by directly linking at least one monocyclic and/or condensed-cyclic heteroarylene group to at least one monocyclic and/or condensed-cyclic arylene group at each occurrence or by indirectly linking at least one monocyclic and/or condensed-cyclic heteroarylene group to at least one monocyclic and/or condensed-cyclic arylene group via a hetero atom or a carbonyl group at each occurrence, with a compound represented by the formula (B):

$$Ar^2\text{---}(X^2)_n \tag{B}$$

wherein,

X² represents a chlorine atom, a bromine atom, an iodine atom, an alkylsulfonyloxy group, an alkylsulfonyloxy group substituted with a fluorine atom, or an arylsulfonyloxy group. When a plurality of X² are present, the plurality of X² may be the same or different at each occurrence, n represents 1 or 2, n in the formula (B) may be the same as or different from m in the formula (A), Ar² represents an aryl group having a number of carbon atoms of 6 to 36 and optionally having a substituent or a heteroaryl group having a number of carbon atoms of 4 to 36 and optionally having a substituent when n is 1, Ar² represents an arylene group having a number of carbon atoms of 6 to 36 and optionally having a substituent or a heteroarylene group having a number of carbon atoms of 4 to 36 and optionally having a substituent when n is 2, the number of carbon atoms of these groups does not include the number of carbon atoms of the substituent, the substituent which these groups optionally have is selected from Group 1, the aryl group may be a monovalent group formed by directly linking two or more monocyclic and/or condensed-cyclic aryl groups at each occurrence or by indirectly linking two or more monocyclic and/or condensed-cyclic aryl groups via a hetero atom or a carbonyl group at each occurrence, the heteroaryl group may be a monovalent group formed by directly linking two or more monocyclic and/or condensed-cyclic heteroaryl groups at each occurrence or by indirectly linking two or more monocyclic and/or condensed-cyclic heteroaryl groups via a hetero atom or a carbonyl group at each occurrence, or may be a monovalent group formed by directly linking at least one monocyclic and/or condensed-cyclic heteroaryl group to at least one monocyclic and/or condensed-cyclic aryl group at each occurrence or by indirectly linking at least one monocyclic and/or condensed-cyclic heteroaryl group to at least one monocyclic and/or condensed-cyclic aryl group via a hetero atom or a carbonyl group at each occurrence, the arylene group may be a divalent group formed by directly linking two or more monocyclic and/or condensed-cyclic arylene groups at each occurrence or by indirectly linking two or more monocyclic and/or condensed-cyclic arylene groups via a hetero atom or a carbonyl group at each occurrence, and the heteroarylene group may be a divalent group formed by directly linking two or more monocyclic and/or condensed-cyclic heteroarylene groups at each occurrence or by indirectly linking two or more monocyclic and/or condensed-cyclic heteroarylene groups via a hetero atom or a carbonyl group at each occurrence, or may be a divalent group formed by directly linking at least one monocyclic and/or condensed-cyclic heteroarylene group to at least one monocyclic and/or condensed-cyclic arylene group at each occurrence or by indirectly linking at least one monocyclic and/or condensed-cyclic heteroarylene group to at least one monocyclic and/or condensed-cyclic arylene group via a hetero atom or a carbonyl group at each occurrence, in the presence of a palladium complex represented by the formula (C):

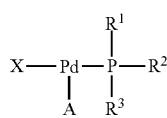

(C)

wherein,

X represents a chlorine atom, a bromine atom or an iodine atom,

A represents an alkyl group having a number of carbon atoms of 1 to 3,

R¹ represents an alkyl group having a number of carbon atoms of 1 to 20, a cycloalkyl group having a number of carbon atoms of 5 to 10, an aryl group having a number of carbon atoms of 6 to 20 and optionally having a substituent or a heteroaryl group having a number of carbon atoms of 4 to 20 and optionally having a substituent, and R² and R³ each independently represent an alkyl group having a number of carbon atoms of 1 to 20 or a cycloalkyl group having a number of carbon atoms of 5 to 10, the number of carbon atoms of the aryl group and the heteroaryl group does not include the number of carbon atoms of the substituent, and the substituent which the aryl group and the heteroaryl group optionally have is selected from Group 1, or the formula (C'):

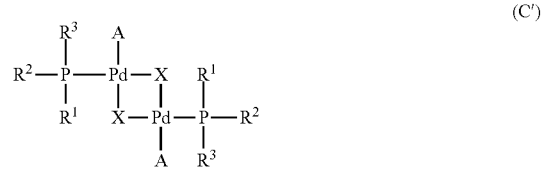

(C')

wherein, X, A, R¹, R² and R³ are the same as defined above, and the plurality of X, A, R¹, R² and R³ may be the same or different at each occurrence.
and a base.

[8] The process for producing the aromatic compound according to [7], wherein R¹ is an aryl group having a number of carbon atoms of 6 to 20 and optionally having a substituent or a heteroaryl group having a number of carbon atoms of 4 to 20 and optionally having a substituent.

[9] The process for producing the aromatic compound according to [7] or [8], wherein R² and R³ each independently represent an alkyl group having a number of carbon atoms of 1 to 6 or a cycloalkyl group having a number of carbon atoms of 5 to 6.

[10] The process for producing the aromatic compound according to any one of [7] to [9], wherein A is a methyl group.

[11] The process for producing the aromatic compound according to any one of [7] to [10], wherein Ar¹ and Ar² each independently represent a group selected from the following Group Ar;

Group Ar:

a monocyclic aryl group, a condensed-cyclic aryl group and a monovalent group formed by directly linking two or more monocyclic aryl groups at each occurrence or by indirectly linking two or more monocyclic aryl groups via a hetero atom or a carbonyl group at each occurrence, a monocyclic heteroaryl group, a condensed-cyclic heteroaryl group and a monovalent group formed by directly linking two or more monocyclic heteroaryl groups at each occurrence or by indirectly linking two or more monocyclic heteroaryl groups via a hetero atom or a carbonyl group at each occurrence, a monocyclic arylene group, a condensed-cyclic arylene group and a divalent group formed by directly linking two or more monocyclic arylene groups at each occurrence or by indirectly linking two or more monocyclic arylene groups via a hetero atom or a carbonyl group at each occurrence, and a monocyclic heteroarylene group, a condensed-cyclic heteroarylene group and a divalent group formed by directly linking two or more monocyclic heteroarylene groups at each occurrence or by indirectly linking two or more monocyclic heteroarylene groups via a hetero atom or a carbonyl group at each occurrence.

[12] A palladium complex represented by the formula (C):

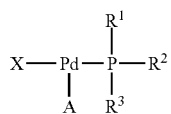

(C)

wherein,

X represents a chlorine atom, a bromine atom or an iodine atom,

A represents an alkyl group having a number of carbon atoms of 1 to 3, $R^1$ represents an alkyl group having a number of carbon atoms of 1 to 20, a cycloalkyl group having a number of carbon atoms of 5 to 10, an aryl group having a number of carbon atoms of 6 to 20 and optionally having a substituent or a heteroaryl group having a number of carbon atoms of 4 to 20 and optionally having a substituent, and $R^2$ and $R^3$ each independently represent an alkyl group having a number of carbon atoms of 1 to 20 or a cycloalkyl group having a number of carbon atoms of 5 to 10, the number of carbon atoms of the aryl group and the heteroaryl group does not include the number of carbon atoms of the substituent, and the substituent which the aryl group and the heteroaryl group optionally have is selected from Group 1, or the formula (C'):

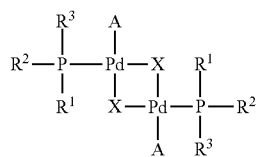

(C')

wherein, X, A, $R^1$, $R^2$ and $R^3$ are the same as defined above, the plurality of X, A, $R^1$, $R^2$ and $R^3$ may be the same or different at each occurrence, wherein the complex is a catalyst for the Suzuki coupling.

[13] The palladium complex according to [12], wherein $R^1$ is an aryl group having a number of carbon atoms of 6 to 20 and optionally having a substituent or a heteroaryl group having a number of carbon atoms of 4 to 20 and optionally having a substituent.

[14] The palladium complex according to [12] or [13], wherein $R^2$ and $R^3$ each independently represent an alkyl group having a number of carbon atoms of 1 to 6 or a cycloalkyl group having a number of carbon atoms of 5 to 6.

[15] The palladium complex according to any one of to [14], wherein A is a methyl group.

Effect of the Invention

The present invention can provide a process for producing an aromatic compound in a high yield and a catalyst used in the process.

Modes for Carrying Out the Invention

The present invention will be illustrated in detail below.
<Explanation of Common Terms>

The terms commonly used in the present specification have the following meanings unless otherwise stated.

The alkyl group may be linear or branched. The alkyl group has a number of carbon atoms of usually 1 to 20. Specific examples of the alkyl group include a methyl group, an ethyl group, a n-propyl group, an isopropyl group, a n-butyl group, an isobutyl group, a sec-butyl group, a tert-butyl group, a n-pentyl group, a 2,2-dimethylpropyl group, a cyclopentyl group, a n-hexyl group, a cyclohexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl group.

The alkyl group substituted with a fluorine atom is an alkyl group having a fluorine atom as the substituent. The alkyl group is the same as defined above.

The cycloalkyl group has a number of carbon atoms of usually 3 to 20. Specific examples of the cycloalkyl group include a cyclopropyl group, a cyclopentyl group, a cyclohexyl group, a cycloheptyl group and a cyclooctyl group.

The alkoxy group may be linear or branched. The alkoxy group has a number of carbon atoms of usually 1 to 20. Specific examples of the alkoxy group include a methoxy group, an ethoxy group, a n-propoxy group, an isopropoxy group, a n-butoxy group, a sec-butoxy group, a tert-butoxy group, a n-pentyloxy group, a 2,2-dimethylpropoxy group, a n-hexyloxy group, a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group and a n-icosyloxy group.

The cycloalkoxy group has a number of carbon atoms of usually 3 to 20. Specific examples of the cycloalkoxy group include a cyclopropoxy group, a cyclopentyloxy group, a cyclohexyloxy group, a cycloheptyloxy group and a cyclooctyloxy group.

The alkylthio group has a number of carbon atoms of usually 1 to 20. Specific examples of the alkylthio group include a methylthio group, an ethylthio group, a n-propylthio group, an isopropylthio group, a n-butylthio group, an isobutylthio group, a sec-butylthio group, a tert-butylthio group, a n-pentylthio group, a n-hexylthio group, a n-heptylthio group, a n-octylthio group, a 2-ethylhexylthio group, a n-nonylthio group, a n-decylthio group, a 3,7-dimethyloctylthio group and a n-dodecylthio group.

In the cycloalkylthio group, the cycloalkyl group has a number of carbon atoms of usually 3 to 20. Specific examples of the cycloalkylthio group include a cyclopropylthio group, a cyclopentylthio group, a cyclohexylthio group, a cycloheptylthio group and a cyclooctylthio group.

The aryl group is a group generated by elimination of one hydrogen atom linking to the ring of an aromatic hydrocarbon. The aryl group has a number of carbon atoms of usually 6 to 20. Specific examples of the aryl group include a phenyl group, a 4-methylphenyl group, a 2-methylphenyl group, a 2,6-dimethylphenyl group, a 1-naphthyl group, a 2-naphthyl group, a 3-phenanthryl group, a 2-anthryl group and the like.

The aryloxy group is a group obtained by linking an aryl group to an oxy group, and the aryl group has a number of carbon atoms of usually 6 to 20. Specific examples of the aryloxy group include a phenoxy group, a naphthyloxy group, a phenanthryloxy group, and an anthryloxy group.

In the arylthio group, the aryl group has a number of carbon atoms of usually 6 to 20. Specific examples of the arylthio group include a phenylthio group, and a naphthylthio group.

The arylalkyl group is an alkyl group having an aryl group as the substituent, and the aryl group has a number of carbon atoms of usually 6 to 20 and the alkyl group has a number of carbon atoms of usually 1 to 20.

The arylcycloalkyl group is a cycloalkyl group having an aryl group as the substituent, and the aryl group has a number of carbon atoms of usually 6 to 20 and the cycloalkyl group has a number of carbon atoms of usually 3 to 20.

The alkenyl group has a number of carbon atoms of usually 2 to 8. Specific examples of the alkenyl group include a vinyl group, a 1-propenyl group, a 2-propenyl group, a 1-butenyl group, a 2-butenyl group, a 1-pentenyl group, a 2-pentenyl group, a 1-hexenyl group, a 2-hexenyl group and a 1-octenyl group.

The arylalkenyl group is an alkenyl group having an aryl group as the substituent, and the aryl group has a number of carbon atoms of usually 6 to 20 and the alkenyl group group has a number of carbon atoms of usually 2 to 8. Specific examples of the arylalkenyl group include a phenylalkenyl group, and a naphthylalkenyl group The alkynyl group has a number of carbon atoms of usually 2 to 8. Specific examples of the alkynyl group include an ethynyl group, a 1-propynyl group, a 2-propynyl group, a 1-butynyl group, a 2-butynyl group, a 1-pentynyl group, a 2-pentynyl group, a 1-hexynyl group, a 2-hexynyl group and a 1-octynyl group.

The arylalkynyl group is an alkynyl group having an aryl group as the substituent, and the aryl group has a number of carbon atoms of usually 6 to 20 and the alkenyl group group has a number of carbon atoms of usually 2 to 8. Specific examples of the arylalkynyl group include a phenylalkynyl group, and a naphthylalkynyl group.

The heterocycle group is an atomic group remaining after removing from a heterocyclic compound one hydrogen atom directly linking to a carbon atom constituting the ring, and the heterocycle group has a number of carbon atoms of usually 3 to 20. Specific examples of the heterocycle group include a thienyl group, a pyrrolyl group, a furyl group, a pyridyl group, a pyridazinyl group, a pyrimidinyl group, a pyrazinyl group, a triazinyl group, a pyrrolidinyl group, a piperidinyl group, a quinolyl group, and an isoquinolyl group. The heterocycle group may have an alkyl group as the substituent.

In the group represented by —N(R')$_2$ wherein two R' each independently represent a hydrogen atom, a hydrocarbon group having a number of carbon atoms of 1 to 20 or a heterocycle group having a number of carbon atoms of 3 to 20 optionally having an alkyl group, the hydrocarbon group having a number of carbon atoms of 1 to 20 represented by R' includes an alkyl group, a cycloalkyl group, and an aryl group. In the group represented by —N(R')$_2$, it is preferable that at least one R' is a hydrocarbon group having a number of carbon atoms of 1 to 20 or a heterocycle group optionally having an alkyl group.

Specific examples of the group represented by —N(R')$_2$ include a methylamino group, a dimethylamino group, an ethylamino group, a diethylamino group, a n-propylamino group, a di-n-propylamino group, an isopropylamino group, a diisopropylamino group, a n-butylamino group, an isobutylamino group, a sec-butylamino group, a tert-butylamino group, a n-pentylamino group, a n-hexylamino group, a n-heptylamino group, a n-octylamino group, a 2-ethylhexylamino group, a n-nonylamino group, a n-decylamino group, a 3,7-dimethyloctylamino group, a n-dodecylamino group, a cyclopentylamino group, a dicyclopentylamino group, a cyclohexylamino group, a dicyclohexylamino group, a bis(trifluoromethyl)amino group, a phenylamino group, a diphenylamino group, a naphthylamino group, a pyridylamino group, a pyridazinylamino group, a pyrimidinylamino group, a pyrazinylamino group and a triazinylamino group.

In the group represented by —Si(R')$_3$ wherein R' is the same as defined above and three R' may be the same or different at each occurrence, it is preferable that at least one R' is a hydrocarbon group having a number of carbon atoms of 1 to 20 or a heterocycle group optionally having an alkyl group.

Specific examples of the group represented by —Si(R')$_3$ include a trimethylsilyl group, a triethylsilyl group, a tri-n-propylsilyl group, a triisopropylsilyl group, a dimethylisopropylsilyl group, a diethylisopropylsilyl group, a tert-butylsilyldimethylsilyl group, a n-pentyldimethylsilyl group, a n-hexyldimethylsilyl group, a n-heptyldimethylsilyl group, a n-octyldimethylsilyl group, a 2-ethylhexyldimethylsilyl group, a n-nonyldimethylsilyl group, a n-decyldimethylsilyl group, a 3,7-dimethyloctyldimethylsilyl group, a n-dodecyldimethylsilyl group, a phenylalkylsilyl group, an alkoxyphenylalkylsilyl group, an alkylphenylalkylsilyl group, a naphthylalkylsilyl group, a phenylallyldimethylsilyl group, a triphenylsilyl group, a tri-p-xylylsilyl group, a tribenzylsilyl group, a diphenylmethylsilyl group, a tert-butyldiphenylsilyl group and a dimethylphenylsilyl group.

The acyl group is represented by R'CO—. R' is the same as defined above. Specific examples of the acyl group include aliphatic acyl groups such as an acetyl group, a propionyl group, a butyryl group, and an isobutyryl group, and aromatic acyl groups such as a benzoyl group and a naphthoyl group.

The group having a carbon atom-nitrogen atom double bond is an atomic group generated by elimination of one hydrogen atom directly linking to a carbon atom or a nitrogen atom constituting the carbon atom-nitrogen atom double bond in the imine compound. The imine compound includes, for example, aldimines, ketimines, and compounds in which a nitrogen atom constituting a carbon atom-nitrogen atom double bond in an aldimine has, as the substituent, an alkyl group, an aryl group, an arylalkyl group, an arylalkenyl group or an arylalkynyl group.

The group having a carbon atom-nitrogen atom double bond includes a group represented by —CR"=N—R'" and a group represented by —N=C(R'")$_2$. R" represents a hydrogen atom, an alkyl group, an aryl group, an arylalkyl group, an arylalkenyl group or an arylalkynyl group. One or two R'" each independently represent an alkyl group, a cycloalkyl group, an aryl group, an arylalkyl group, an arylcycloalkyl group, an arylalkenyl group or an arylalkynyl group. In the group represented by —N=C(R'")$_2$, two R'" are combined together to form a divalent group, specifically, alkylene groups having a number of carbon atoms of 2 to 18 such as an ethylene group, a trimethylene group, a tetramethylene group, a pentamethylene group, and a hexamethylene group.

The group having a carbon atom-nitrogen atom double bond has a number of carbon atoms of usually 2 to 20, preferably 2 to 18, more preferably 2 to 16.

Specific examples of "the group having a carbon atom-nitrogen atom double bond" include groups shown below.

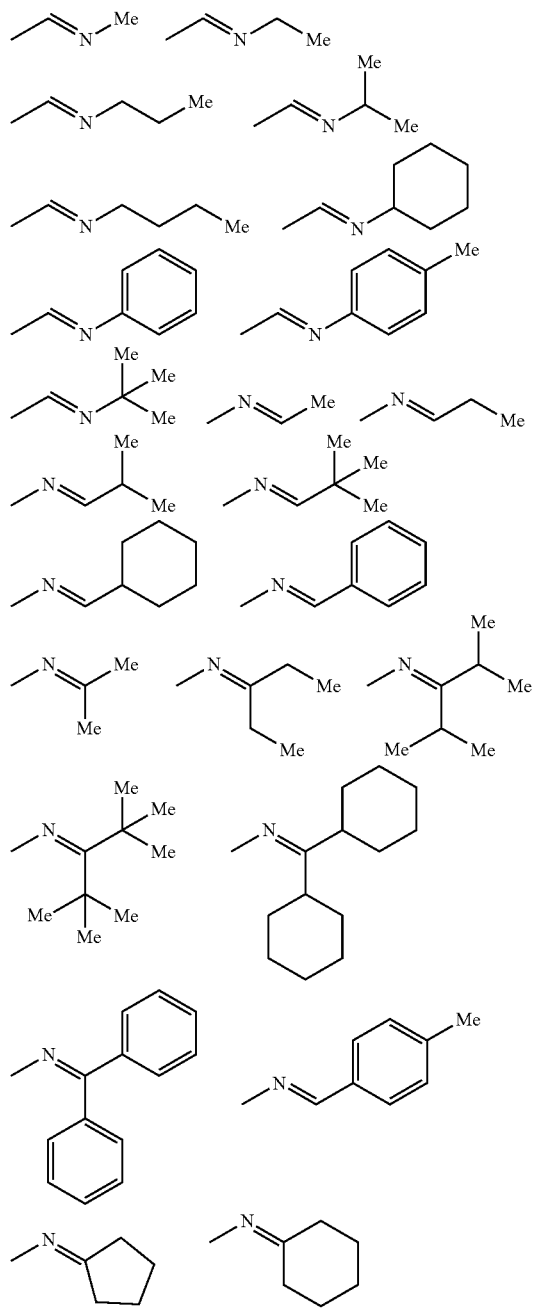

The acid imide group is represented by (R'CO)$_2$N—. R' is the same as defined above and two R' may be the same or different at each occurrence. Two R' may be combined each other to form a ring together with a carbon atom to which they link and with a nitrogen atom linking to this carbon atom. The acid imide group has a number of carbon atoms of preferably 4 to 20, more preferably 4 to 18, further preferably 4 to 16.

Specific examples of the acid imide group include groups shown below.

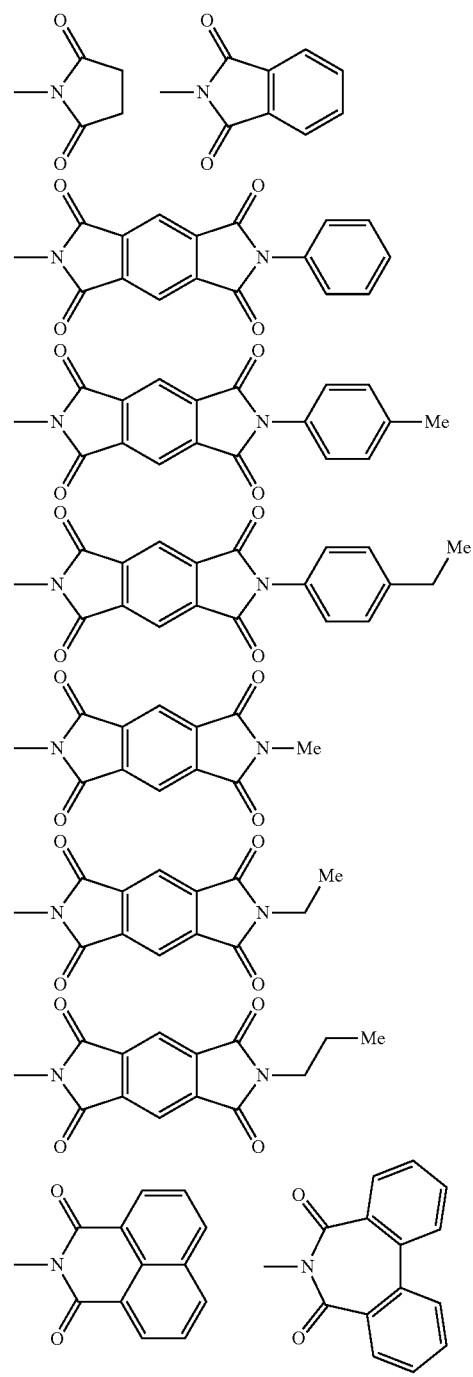

The alkoxycarbonyl group is a group obtained by linking an alkoxy group to a carbonyl group. The alkoxy group is the same as defined above. Specific examples of the alkoxycarbonyl group include a methoxycarbonyl group, an ethoxycarbonyl group, a n-propoxycarbonyl group, an isopropoxycarbonyl group, a n-butoxycarbonyl group, an isobutoxycarbonyl group, a sec-butoxycarbonyl group, a tert-butoxycarbonyl group, a n-pentyloxycarbonyl group, a n-hexyloxycarbonyl group, a n-heptyloxycarbonyl group, a n-octyloxycarbonyl group, a 2-ethylhexyloxycarbonyl group, a n-nonyloxycarbonyl group, a n-decyloxycarbonyl group, a 3,7-dimethyloctyloxycarbonyl group, a n-dodecyloxycarbonyl group, a trifluoromethoxycarbonyl group, a pentafluoroethoxycarbonyl group, a perfluorobutoxycarbonyl group, a perfluorohexyloxycarbonyl group and a perfluorooctyloxycarbonyl group.

The cycloalkoxycarbonyl group is a group obtained by linking a cycloalkoxy group to a carbonyl group. The cycloalkoxy group is the same as defined above. Specific examples of the cycloalkoxycarbonyl group include a cyclohexyloxycarbonyl group.

The aryloxycarbonyl group is a group obtained by linking an aryloxy group to a carbonyl group. The aryloxy group is the same as defined above. Specific examples of the aryloxycarbonyl group include a phenoxycarbonyl group, a naphthoxycarbonyl group and a pyridyloxycarbonyl group.

The alkylsulfonyloxy group is a group obtained by linking an alkylsulfonyl group to an oxy group. The alkyl group which the alkylsulfonyl group has is the same as defined above. Specific examples of the alkylsulfonyloxy group include an oxymethanesulfonyloxy group.

The alkylsulfonyloxy group substituted with a fluorine atom is a group obtained by linking a fluorine-substituted alkylsulfonyl group to an oxy group. The alkyl group substituted with a fluorine atom which the alkylsulfonyl group substituted with a fluorine atom has is the same as defined above. Specific examples of the fluorine-substituted alkylsulfonyloxy group include a trifluoromethanesulfonyloxy group.

The arylsulfonyloxy group is a group obtained by linking an arylsulfonyl group to an oxy group. The arylsulfonyl group is a group obtained by linking an aryl group to a sulfonyl group. The aryl group is the same as defined above. Specific examples of the arylsulfonyloxy group include a p-toluenesulfonyloxy group.

The aryl group having a number of carbon atoms of 6 to 36 includes monocyclic aryl groups, condensed-cyclic aryl groups and monovalent groups formed by directly linking two or more monocyclic and/or condensed-cyclic aryl groups at each occurrence or by indirectly linking two or more monocyclic and/or condensed-cyclic aryl groups via a hetero atom such as oxygen atom, nitrogen atom and sulfur atom or a carbonyl group (—CO—) at each occurrence. The remaining linking bond of a nitrogen atom for indirectly linking an aryl group is linked to, for example, an alkyl group and optionally having a substituent and an aryl group and optionally having a substituent.

The monocyclic aryl group includes a phenyl group. The condensed-cyclic aryl group includes a naphthyl group, an anthracenyl group and a fluorenyl group. The monovalent group formed by directly linking two or more monocyclic aryl groups at each occurrence or by indirectly linking two or more monocyclic aryl groups via a hetero atom or a carbonyl group at each occurrence includes a biphenyl group.

The aryl group having a number of carbon atoms of 6 to 36 includes groups represented by the formula (a-1) to the formula (e-1) and the formula (k-1) to the formula (o-1),

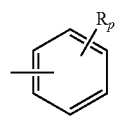
(a-1)

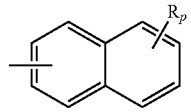
(b-1)

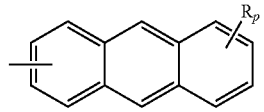
(c-1)

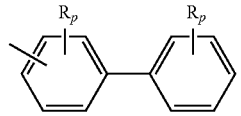
(d-1)

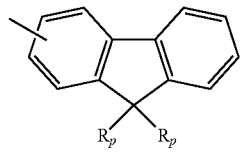
(e-1)

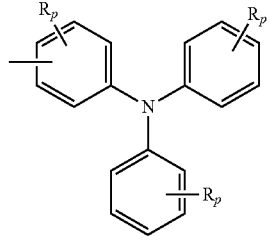
(k-1)

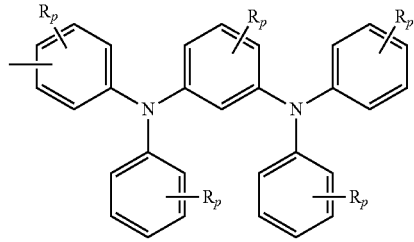
(l-1)

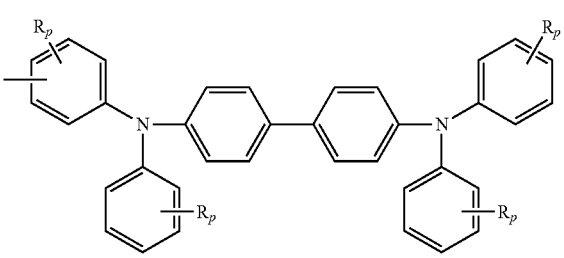
(m-1)

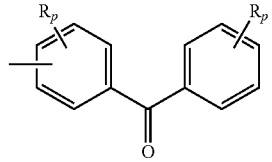
(n-1)

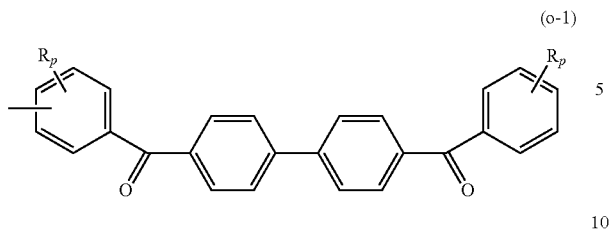

(o-1)

wherein, R represents a substituent selected from Group 1. p represents an integer of 0 to 4.

The arylene group having a number of carbon atoms of 6 to 36 includes monocyclic arylene groups, condensed-cyclic arylene groups, and divalent groups formed by directly linking two or more monocyclic and/or condensed-cyclic arylene groups at each occurrence or by indirectly linking two or more monocyclic and/or condensed-cyclic arylene groups via a hetero atom such as oxygen atom, nitrogen atom and sulfur atom or a carbonyl group (—CO—) at each occurrence. The remaining linking bond of a nitrogen atom for indirectly linking an aryl group is linked to, for example, an alkyl group and optionally having a substituent and an aryl group and optionally having a substituent. The monocyclic arylene group includes a phenylene group. The condensed-cyclic arylene group includes a naphthalenediyl group, an anthracenediyl group and a fluorenediyl group. The divalent group formed by directly linking two or more monocylic arylene groups at each occurrence or by indirectly linking two or more monocylic arylene groups via a hetero atom or a carbonyl group at each occurrence includes a biphenylene group.

The arylene group having a number of carbon atoms of 6 to 36 includes groups represented by the formula (a-2) to the formula (e-2) and the formula (k-2) to the formula (o-2),

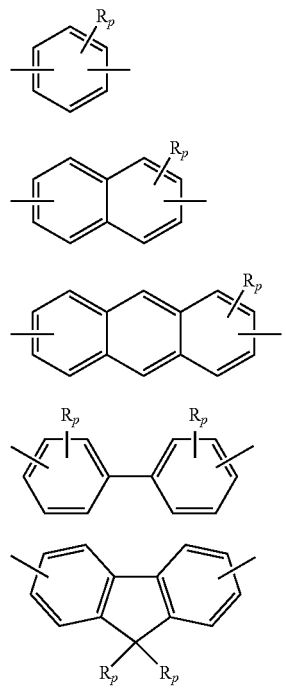

(a-2)

(b-2)

(c-2)

(d-2)

(e-2)

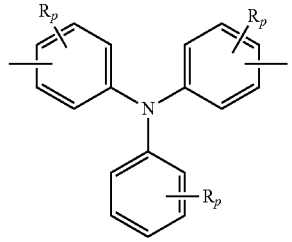

(k-2)

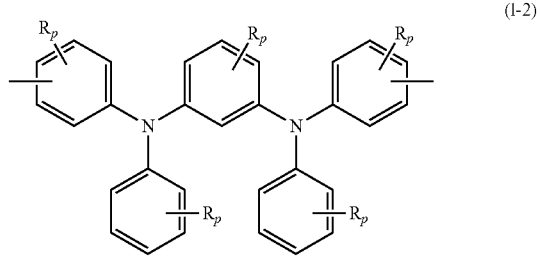

(l-2)

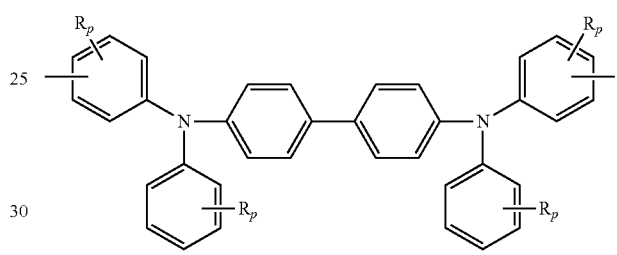

(m-2)

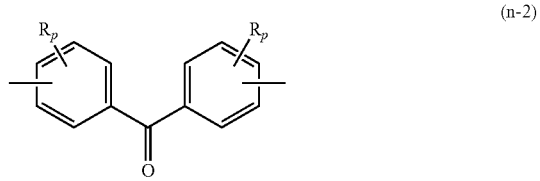

(n-2)

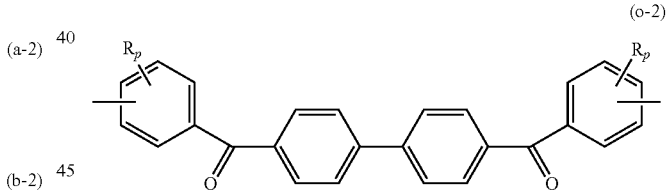

(o-2)

wherein, R and p is the same as defined above.

The heteroaryl group is a group in which a carbon atom constituting the ring of an aryl group is replaced by a hetero atom or a carbonyl group.

The heteroaryl group having a number of carbon atoms of 4 to 36 includes monocyclic heteroaryl groups, condensed-cyclic heteroaryl groups, monovalent groups formed directly linking two or more monocyclic and/or condensed-cyclic heteroaryl groups at each occurrence or by indirectly linking two or more monocyclic and/or condensed-cyclic heteroaryl groups via a hetero atom such as oxygen atom, nitrogen atom and sulfur atom or a carbonyl group (—CO—) at each occurrence, and monovalent groups formed by directly linking at least one monocyclic and/or condensed-cyclic heteroaryl group to at least one monocyclic and/or condensed-cyclic aryl group at each occurrence or by indirectly linking at least one monocyclic and/or condensed-cyclic heteroaryl group to at least one monocyclic and/or condensed-cyclic aryl group via a hetero atom such as oxygen atom, nitrogen atom and sulfur atom or a carbonyl group (—CO—) at each occurrence. The remaining linking bond of a nitrogen atom for indirectly linking a heteroaryl group is linked to, for example, an alkyl group and optionally having a substituent and an aryl group and optionally having a substituent. The condensed ring contained in the condensed-cyclic heteroaryl group may be a condensed ring in which two or more heterocycles are condensed or at least one heterocycle and at least one aromatic ring are condensed.

The heteroaryl group having a number of carbon atoms of 4 to 36 includes groups represented by the formula (f-1) to the formula (i-1) and the formula (p-1) to the formula (r-1),

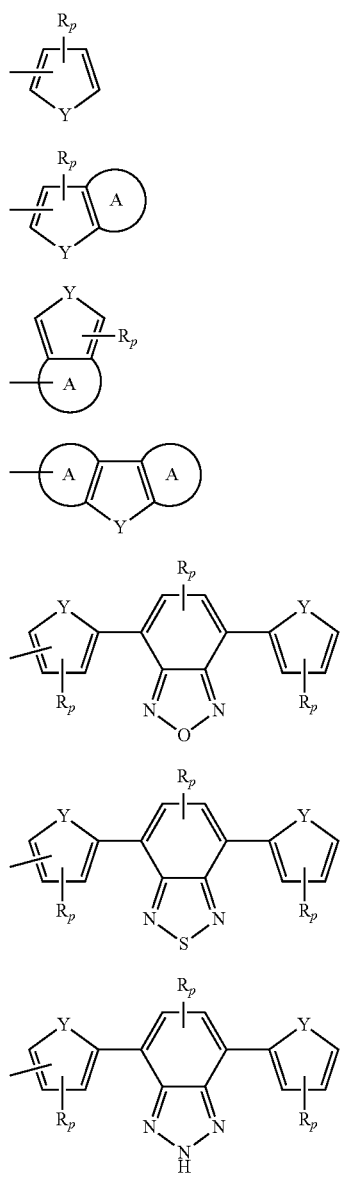

wherein, R and p are the same as defined above. Y represents a sulfur atom, an oxygen atom or a group represented by —$NR^Y$—. $R^Y$ represents a hydrogen atom, an alkyl group and optionally having a substituent or an aryl group and optionally having a substituent. Ring A represents a heterocycle or an aromatic ring.

The groups represented by the formulae (f-1) to (i-1) include groups represented by the formula (fa-1) to the formula (im-1), respectively,

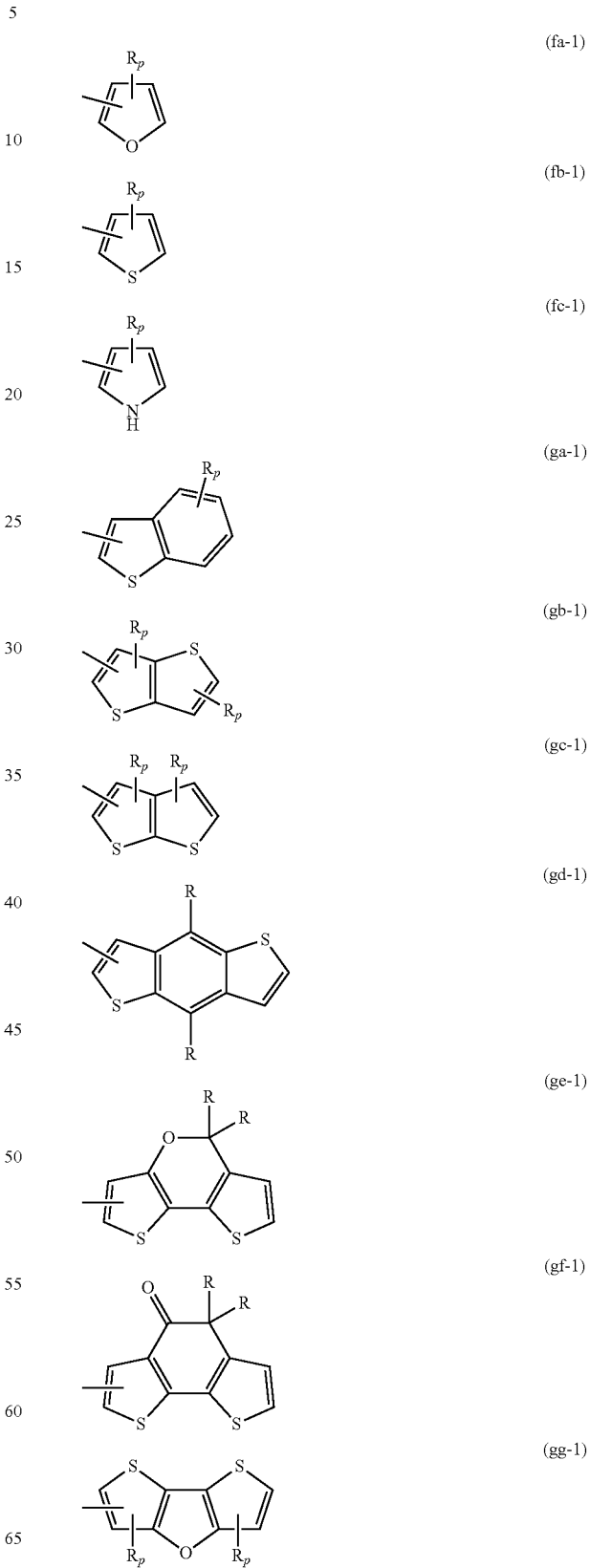

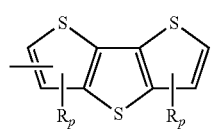 (gh-1)
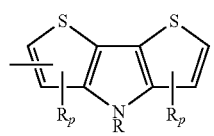 (gi-1)
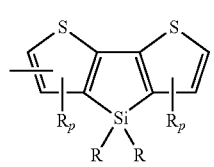 (gj-1)
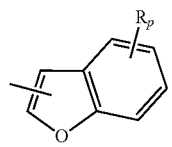 (gk-1)
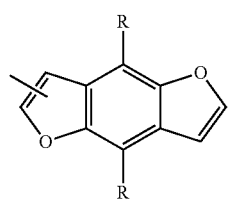 (gl-1)
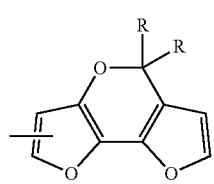 (gm-1)
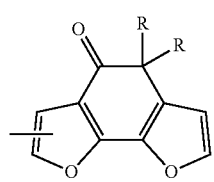 (gn-1)
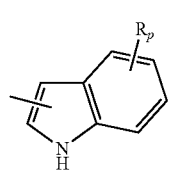 (go-1)
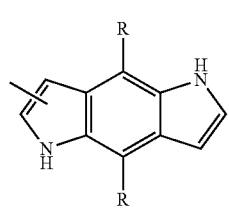 (gp-1)
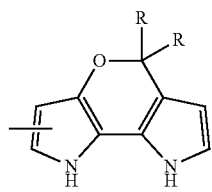 (gq-1)
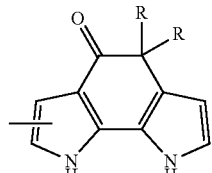 (gr-1)
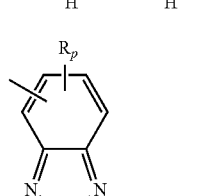 (ha-1)
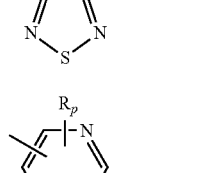 (hb-1)
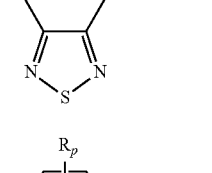 (hc-1)
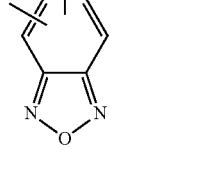 (hd-1)
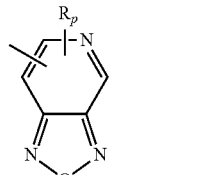 (he-1)
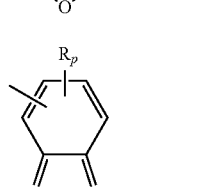 (hf-1)

-continued

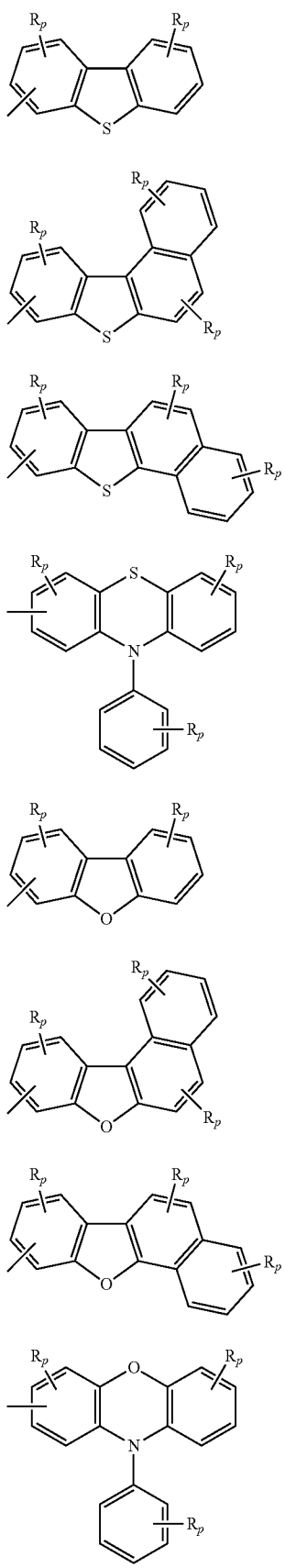

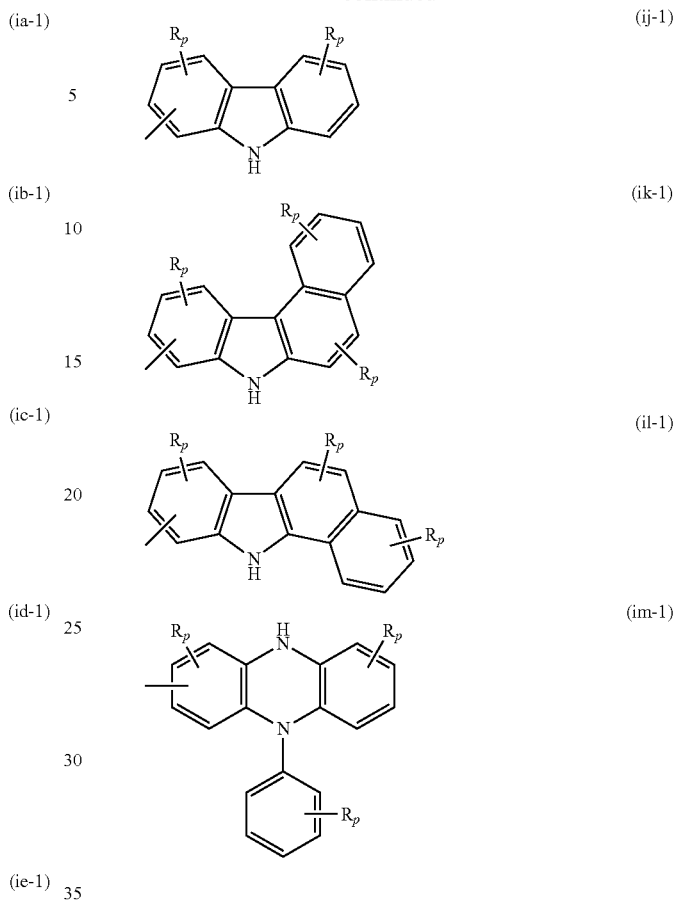

wherein, R and p are the same as defined above.

The heteroarylene group is a group in which a carbon atom constituting the ring of an arylene group is substituted with a hetero atom or a carbonyl group.

The heteroarylene group having a number of carbon atoms of 4 to 36 includes monocyclic heteroarylene groups, condensed-cyclic heteroarylene groups, divalent groups formed by directly linking two or more monocyclic and/or condensed-cyclic heteroarylene groups at each occurrence or by indirectly linking two or more monocyclic and/or condensed-cyclic heteroarylene groups via a hetero atom such as oxygen atom, nitrogen atom and sulfur atom or a carbonyl group (—CO—) at each occurrence, and divalent groups formed by directly linking at least one monocyclic and/or condensed-cyclic heteroarylene group to at least one monocyclic and/or condensed-cyclic arylene group at each occurrence or by indirectly linking at least one monocyclic and/or condensed-cyclic heteroarylene group to at least one monocyclic and/or condensed-cyclic arylene group via a hetero atom such as oxygen atom, nitrogen atom and sulfur atom or a carbonyl group (—CO—) at each occurrence. The remaining linking bond of a nitrogen atom for indirectly linking a heteroarylene group is linked to, for example, an alkyl group and optionally having a substituent and an aryl group and optionally having a substituent. The condensed ring contained in the condensed-cyclic heteroaryl group may be a condensed ring in which two or more heterocycles are condensed or a condensed ring comprising at least one heterocycle and at least one aromatic ring are condensed.

The heteroarylene group having a number of carbon atoms of 4 to 36 includes groups represented by the formula (f-2) to the formula (i-2) and the formula (p-2) to the formula (r-2), respectively,

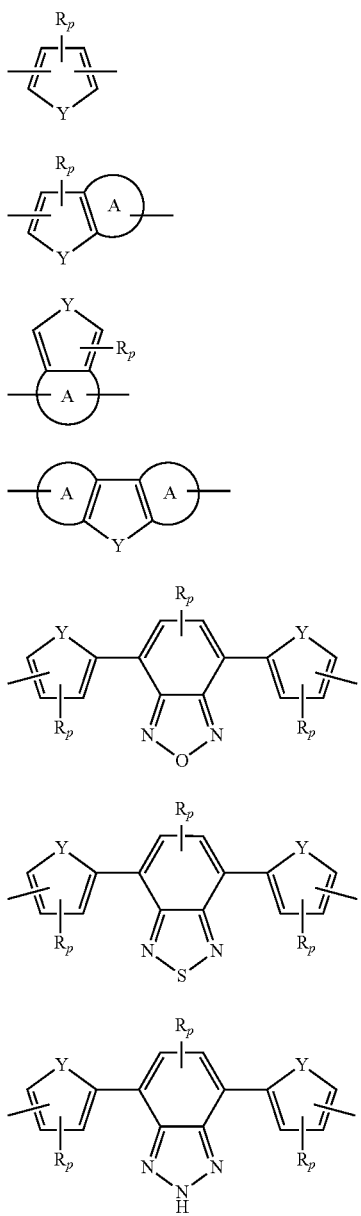
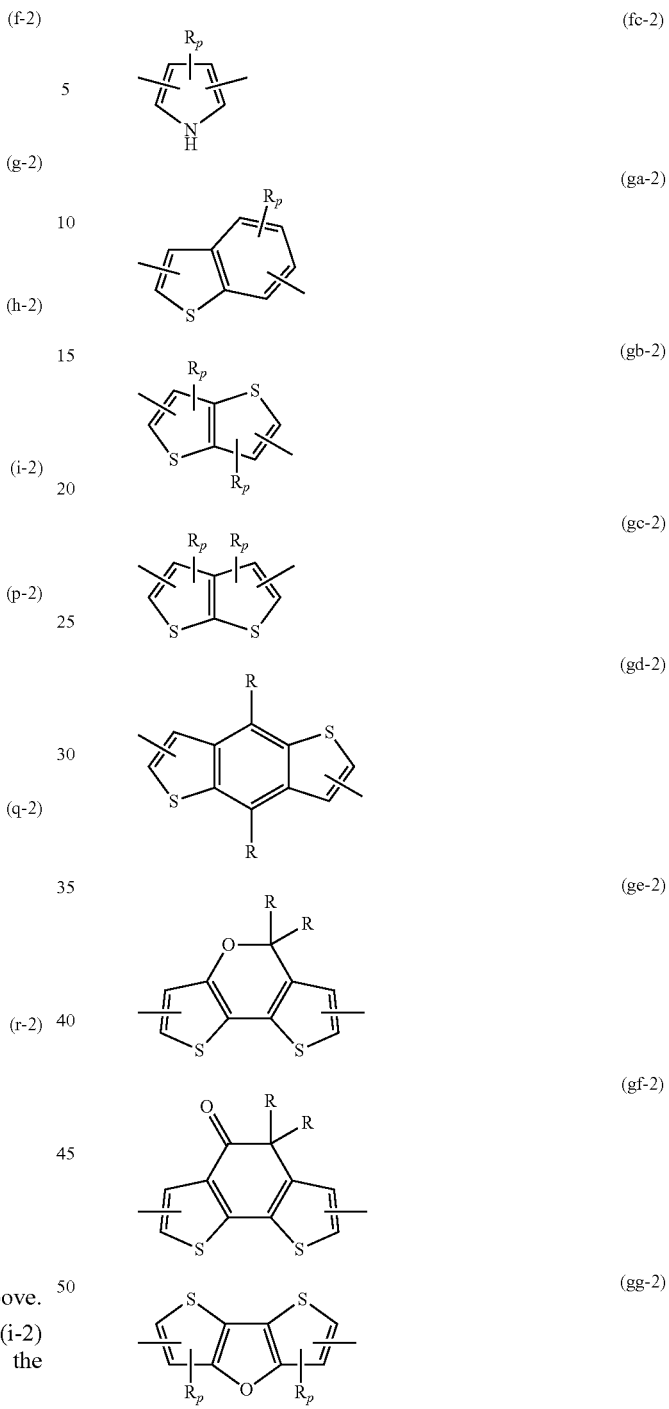
wherein, R, p, Y and Ring A are the same as defined above.
The groups represented by the formulae (f-2) to (i-2) include groups represented by the formula (fa-2) to the formula (im-2), respectively,
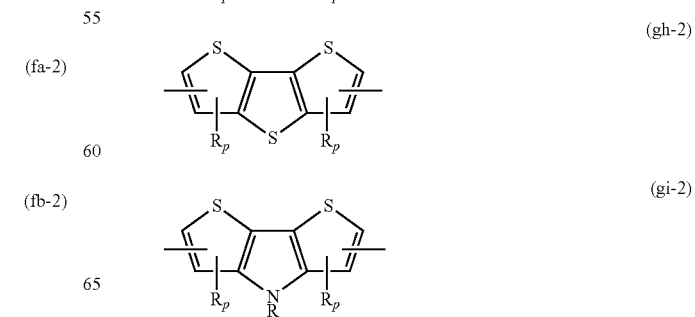

-continued
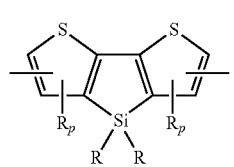
(gj-2)
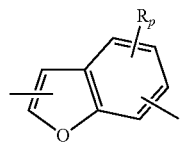
(gk-2)
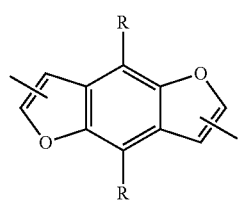
(gl-2)
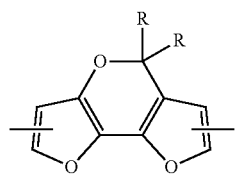
(gm-2)
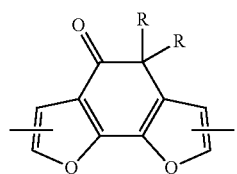
(gn-2)
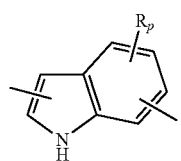
(go-2)
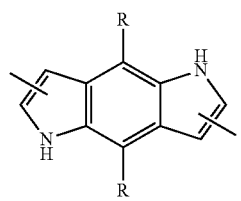
(gp-2)
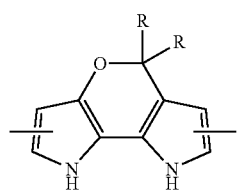
(gq-2)
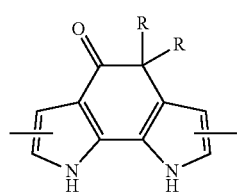
(gr-2)
-continued
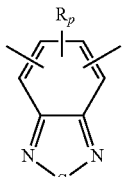
(ha-2)
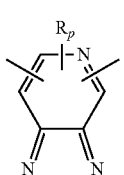
(hb-2)
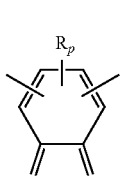
(hc-2)
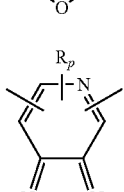
(hd-2)
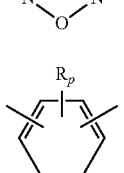
(he-2)
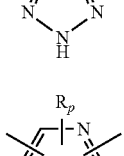
(hf-2)
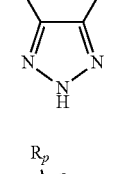
(ia-2)
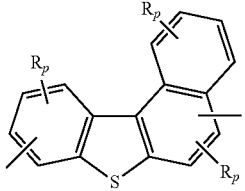
(ib-2)

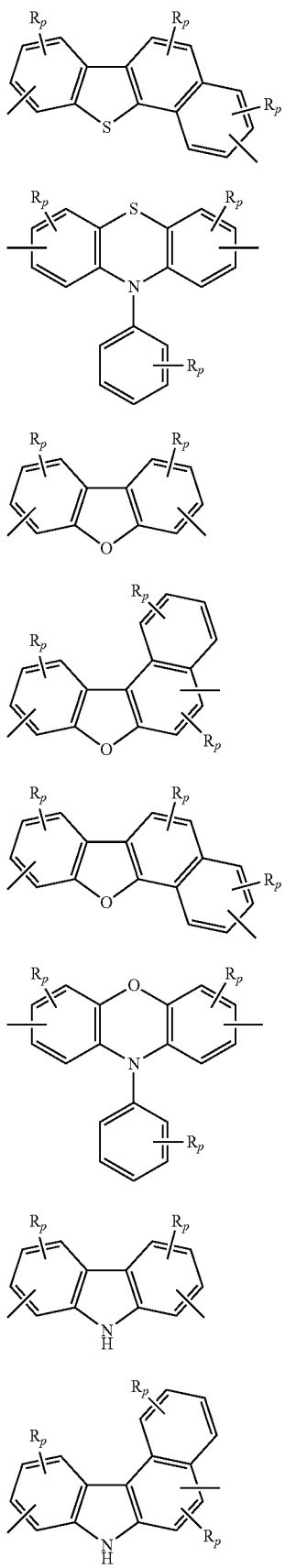

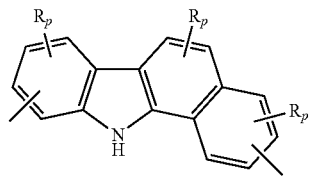

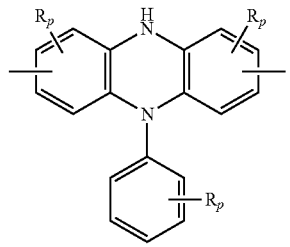

wherein, R and p are the same as defined above.

As the substituent in Group 1, a fluorine atom, an alkyl group, a cycloalkyl group, an alkoxy group, a cycloalkoxy group, an alkylthio group, a cycloalkylthio group, an aryl group, an aryloxy group, an arylthio group, an arylalkyl group, an arylcycloalkyl group, an arylalkenyl group, an arylalkynyl group, a heterocycle group optionally having an alkyl group, a group represented by —N(R')$_2$ wherein tow R' each independently represent a hydrogen atom, a hydrocarbon group having a number of carbon atoms of 1 to 20 or a heterocycle group having a number of carbon atoms of 3 to 20 optionally having an alkyl group, a group represented by —Si(R')$_3$ wherein R' is the same as defined above and three R' may be the same or different at each occurrence, an acyl group, an alkoxycarbonyl group, an aryloxycarbonyl group and a carboxy group are preferable, a fluorine atom, an alkyl group, a cycloalkyl group, an alkoxy group, an alkylthio group, an aryl group, a heterocycle group optionally having an alkyl group, a group represented by —N(R')$_2$ wherein two R' each independently represent a hydrogen atom, a hydrocarbon group having a number of carbon atoms of 1 to 20 or a heterocycle group having a number of carbon atoms of 3 to 20 optionally having an alkyl group, a group represented by —Si(R')$_3$ wherein R' is the same as defined above and three R' may be the same or different at each occurrence, an acyl group, an alkoxycarbonyl group, an aryloxycarbonyl group and a carboxy group are more preferable, a fluorine atom, an alkyl group, a cycloalkyl group, an alkoxy group, an alkylthio group and an aryl group are still more preferable.

<Compound Represented by the Formula (A)>

In the process of the present invention, a compound represented by the formula (A) is used.

$$Ar^1\!\!-\!\!(X^1)_m \quad (A)$$

In the formula (A), m represents 1 or 2, preferably 2.

In the formula (A), X$^1$ is a group represented by any of the formula (1) to the formula (12).

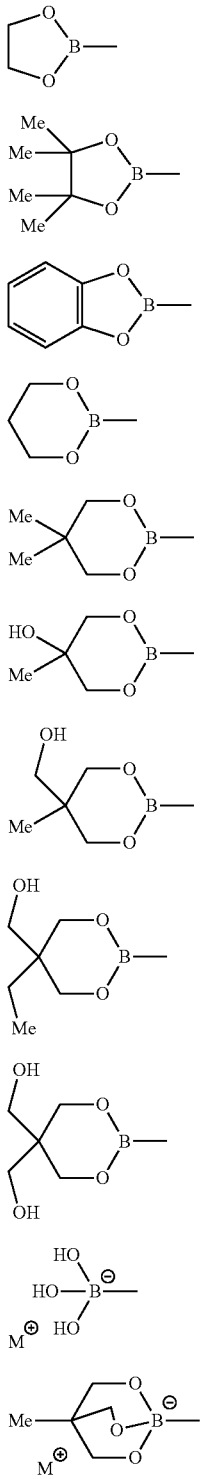

In the formula (A), $X^1$ is preferably a group represented by the formula (1), (2), (3), (8) or (9).

When m is 1 in the formula (A), $Ar^1$ is preferably a group represented by the formula (a-1), (b-1), (c-1), (d-1), (e-1), (f-1), (g-1), (h-1), (p-1), (q-1) or (r-1) wherein Y in the formulae (f-1), (g-1), (h-1), (p-1), (q-1) and (r-1) is preferably S, more preferably a group represented by the formula (g-1), (h-1), (p-1), (q-1) or (r-1) wherein Y in the formulae is preferably S, still more preferably a group represented by the formula (fa-1), (gb-1), (gc-1), (gd-1), (ge-1), (gf-1), (gg-1), (gh-1), (gi-1), (gj-1), (ha-1) or (hb-1).

When m is 2 in the formula (A), $Ar^1$ is preferably a group represented by the formula (a-2), (b-2), (c-2), (d-2), (e-2), (f-2), (g-2), (h-2), (p-2), (q-2) or (r-2) wherein Y in the formulae (f-2), (g-2), (h-2), (p-2), (q-2) and (r-2) is preferably S, more preferably a group represented by the formula (g-2), (h-2), (p-2), (q-2) or (r-2) wherein Y in the formulae is preferably S, still more preferably a group represented by the formula (fa-2), (gb-2), (gc-2), (gd-2), (ge-2), (gf-2), (gg-2), (gh-2), (gi-2), (gj-2), (ha-2) or (hb-2).

The compound represented by the formula (A) is a compound represented by the formula (A-1) or the formula (A-2). Hereinafter, the compound represented by the formula (A-1) is described as compound (A-1) in some cases and the compound represented by the formula (A-2) is described as compound (A-2) in some cases, $$Ar^1-X^1 \quad (A-1)$$

$$X^1-Ar^1-X^1 \quad (A-2)$$

wherein, $X^1$ and $Ar^1$ are the same as defined above.

The compound represented by the formula (A-1) includes phenylboronic acid, o-tolylboronic acid, m-tolylboronic acid, p-tolylboronic acid, 2,3-dimethylphenylboronic acid, 2,4-dimethylphenylboronic acid, 2,5-dimethylphenylboronic acid, 2,6-dimethylphenylboronic acid, 2,4,6-trimethylphenylboronic acid, 2,3,5,6-tetramethylphenylboronic acid, 2-ethylphenylboronic acid, 4-n-propylphenylboronic acid, 4-isopropylphenylboronic acid, 4-n-butylphenylboronic acid, 4-tert-butylphenylboronic acid, 1-naphthylboronic acid, 2-naphthylboronic acid, 2-biphenylboronic acid, 3-biphenylboronic acid, 4-biphenylboronic acid, 2-fluoro-4-biphenylboronic acid, 2-fluorenylboronic acid, 9-phenanthrenylboronic acid, 9-anthracenylboronic acid, 1-pyrenylboronic acid, 2-trifluoromethylboronic acid, 3-trifluoromethylboronic acid, 4-trifluoromethylboronic acid, 3,5-bis(trifluoromethylboron)phenylboronic acid, 2-methoxyphenylboronic acid, 3-methoxyphenylboronic acid, 4-methoxyphenylboronic acid, 2,4-dimethoxyphenylboronic acid, 2,5-dimethoxyphenylboronic acid, 2,6-dimethoxyphenylboronic acid, 3,4-dimethoxyphenylboronic acid, 2-ethoxyphenylboronic acid, 3-ethoxyphenylboronic acid, 4-ethoxyphenylboronic acid, 2-(benzyloxy)phenylboronic acid, 2-phenoxyphenylboronic acid, 4-phenoxyphenylboronic acid, 3,4-methylenedioxyphenylboronic acid, 2-fluorophenylboronic acid, 3-fluorophenylboronic acid, 4-fluorophenylboronic acid, 2,4-difluorophenylboronic acid, 2,5-difluorophenylboronic acid, 2,6-difluorophenylboronic acid, 3,4-difluorophenylboronic acid, 3,5-difluorophenylboronic acid, 2-formylphenylboronic acid, 3-formylphenylboronic acid, 4-formylphenylboronic acid, 3-formyl-4-methoxyphenylboronic acid, 2-cyanophenylboronic acid, 3-cyanophenylboronic acid, 4-cyanophenylboronic acid, 2-acetylphenylboronic acid, 3-acetylphenylboronic acid, 4-acetylphenylboronic acid, 4-biphenylboronic acid, 3-carboxyphenylboronic acid, 3-aminophenylboronic acid, 2-(N,N-dimethylamino)phenylboronic acid, 3-(N,N-dimethylamino)phenylboronic acid, 4-(N,N-dimethylamino)phenylboronic acid, 2-(N,N-dimethylaminomethyl)phenylboronic acid, furan-2-boronic acid, furan-3-boronic acid, 5-formylfuran-2-boronic acid, 3-formylfuran-2-boronic acid, benzofuran-2-boronic acid, dibenzofuran-4-boronic acid, thiophene-2-boronic acid, thiophene-3-boronic acid, 4-methylthiophene-2-boronic acid, 5-methylthiophene-2-boronic acid, 5-chlorothiophene-2-boronic acid, 2-acetylthiophene-5-boronic acid, 3-formylthiophene-2-boronic acid, benzothiophene-2-boronic acid, benzothiophene-4-boronic acid, 3-methylpyrazole-4-boronic acid, 3,5-dimethylpyrazole-4-boronic acid, thiazole-2-boronic acid, pyridine-3-boronic acid, pyridine-4-boronic acid, pyrimidine-5-boronic acid, quinoline-8-boronic acid, isoquinoline-4-boronic acid, 1,4-benzenediboronic acid, 4,4'-biphenyldiboronic acid, vinylboronic acid and 3-methyl-2-buten-2-ylboronic acid.

The compound represented by the formula (A-2) includes 2,2'-(9,9-dihexyl-9H-fluorene-2,7-diyl)bis(4,4,5,5-tetramethyl-1,3,2-dioxaborolane), 2,2'-(9,9-dioctyl-9H-fluorene-2,7-diyl)bis(4,4,5,5-tetramethyl-1,3,2-dioxaborolane), 2,2'-(9,9-didodecyl-9H-fluorene-2,7-diyl)bis(4,4,5,5-tetramethyl-1,3,2-dioxaborolane), 2,2'-(9-octyl-9H-carbazole-3,6-diyl)bis(1,3,2-dioxaborolane), 2,2'-(2-methyl-5-octyl-1,4-phenylene)bis(4,4,5,5-tetramethyl-1,3,2-dioxaborolane), 2,5-bis(1,3,2-dioxaborolan-2-yl)thiophene, 2,5-bis(1,3,2-dioxaborinan-2-yl)thiophene, 2,5-bis(4,4,5,5,-tetramethyl-1,3,2-dioxaborolan-2-yl)thiophene, 2,5-bis(5,5-dimethyl-1,3,2-dioxaborinan-2-yl)thiophene, 1,1'-bis(1,3,2-dioxaborolan-2-yl)-4,4'-biphenyl, 1,1'-bis(4,4,5,5-tetramethyl-1,3,2-dioxaborolan-2-yl)-4,4'-biphenyl, 1,1'-bis(1,3,2-dioxaborolan-2-yl)-4,4'-biphenyl, 1,1'-bis(5,5-dimethyl-1,3,2-dioxaborinan-2-yl)-4,4'-biphenyl, 5,5'-bis(4,4,5,5-tetramethyl-1,3,2-dioxaborolan-2-yl)-2,2'-bithiophene, 2,5-bis(4,4,5,5-tetramethyl-1,3,2-dioxaborolan-2-yl)-thieno[3,2-b]thiophene, 2,5-bis(4,4,5,5-tetramethyl-1,3,2-dioxaborolan-2-yl)-thieno[2,3-b]thiophene, 4,7-bis(4,4,5,5-tetramethyl-1,3,2-dioxaborolan-2-yl)-2,1,3,-benzothiadiazole, 4,7-bis(4,4,5,5-tetramethyl-1,3,2-dioxaborolan-2-yl)-5,6-difluoro-2,1,3,-benzothiadiazole, 2,2'-(5,5-didodecyl-5H-dithieno[3,2-b:2',3'-d]pyran-2,7-diyl)bis(5-methyl-1,3,2-dioxaborinane-5-methanol), 2,2'-(5,5-bis(3,7-dimethyloctyl)-5H-dithieno[3,2-b:2',3'-d]pyran-2,7-diyl)bis(5-methyl-1,3,2-dioxaborinane-5-methanol), 2,2'-(4,4-dioctyl-4H-cyclopenta[2,1-b:3,4-b']bithiophene-2,6-diyl)bis(5-methyl-1,3,2-dioxaborinane-5-methanol, 2,2'-(4,4-di(3-ethylhexyl)-4H-cyclopenta[2,1-b:3,4-b']bithiophene-2,6-diyl)bis(5-methyl-1,3,2-dioxaborinane-5-methanol, 2,2'-(4,4-dioctyl-4H-silolo[3,2-b:4,5-b']bithiophene-2,6-diyl)bis(5-methyl-1,3,2-dioxaborinane-5-methanol, 2,7-bis(5-methyl-5-hydroxymethyl-1,3,2-dioxaborinan-2-yl)-5,5-dodecylbenzo[2,1-b:3,4-b']dithiophene-4(5H)-one and 2,2'-(4-hexyl-4H-dithieno[3,2-b:2',3'-d]pyrrole-2,6-diyl)bis(5-methyl-1,3,2-dioxaborinane-5-methanol, preferably 2,5-bis(4,4,5,5,-tetramethyl-1,3,2-dioxaborolan-2-yl)thiophene, 1,1'-bis(4,4,5,5-tetramethyl-1,3,2-dioxaborolan-2-yl)-4,4'-biphenyl, 5,5'-bis(4,4,5,5-tetramethyl-1,3,2-dioxaborolan-2-yl)-2,2'-bithiophene, 4,7-bis(4,4,5,5-tetramethyl-1,3,2-dioxaborolan-2-yl)-2,1,3,-benzothiadiazole, 4,7-bis(4,4,5,5-tetramethyl-1,3,2-dioxaborolan-2-yl)-5,6-difluoro-2,1,3,-benzothiadiazole, 2,2'-(5,5-didodecyl-5H-dithieno[3,2-b:2',3'-d]pyran-2,7-diyl)bis(5-methyl-1,3,2-dioxaborinane-5-methanol), 2,2'-(5,5-bis(3,7-dimethyloctyl)-5H-dithieno[3,2-b:2',3'-d]pyran-2,7-diyl)bis(5-methyl-1,3,2-dioxaborinane-5-methanol), 2,2'-(4,4-dioctyl-4H-cyclopenta[2,1-b:3,4-b']bithiophene-2,6-diyl)bis(5-methyl-1,3,2-dioxaborinane-5-methanol, 2,2'-(4,4-di(3-ethylhexyl)-4H-cyclopenta[2,1-b:3,4-b']bithiophene-2,6-diyl)bis(5-methyl-1,3,2-dioxaborinane-5-methanol, 2,2'-(4,4-dioctyl-4H-silolo[3,2-b:4,5-b']bithiophene-2,6-diyl)bis(5-methyl-1,3,2-dioxaborinane-5-methanol, 2,7-bis(5-methyl-5-hydroxymethyl-1,3,2-dioxaborinan-2-yl)-5,5-dodecylbenzo[2,1-b:3,4-b']dithiophene-4(5H)-one and 2,2'-(4-hexyl-4H-dithieno[3,2-b:2',3'-d]pyrrole-2,6-diyl)bis(5-methyl-1,3,2-dioxaborinane-5-methanol, more preferably 5,5'-bis(4,4,5,5-tetramethyl-1,3,2-dioxaborolan-2-yl)-2,2'-bithiophene, 4,7-bis(4,4,5,5-tetramethyl-1,3,2-dioxaborolan-2-yl)-2,1,3,-benzothiadiazole, 4,7-bis(4,4,5,5-tetramethyl-1,3,2-dioxaborolan-2-yl)-5,6-difluoro-2,1,3,-benzothiadiazole, 2,2'-(5,5-didodecyl-5H-dithieno[3,2-b:2',3'-d]pyran-2,7-diyl)bis(5-methyl-1,3,2-dioxaborinane-5-methanol), 2,2'-(5,5-bis(3,7-dimethyloctyl)-5H-dithieno[3,2-b:2',3'-d]pyran-2,7-diyl)bis(5-methyl-1,3,2-dioxaborinane-5-methanol) and 2,7-bis(5-methyl-5-hydroxymethyl-1,3,2-dioxaborinan-2-yl)-5,5-dodecylbenzo[2,1-b:3,4-b']dithiophene-4(5H)-one.

In the formula (11) or (12), M is preferably a lithium element, a sodium element or a potassium element.

In the process of the present invention, two or more kinds of the compounds represented by the formula (A) may be used in combination.

<Compound Represented by the Formula (B)>

In the process of the present invention, a compound represented by the formula (B) is used.

$$Ar^2\text{—}(X^2)_n \qquad (B)$$

In the formula (B), n represents 1 or 2, preferably 2.

In the formula (B), $X^2$ is preferably a chlorine atom, a bromine atom or an iodine atom.

When n is 1 in the formula (B), $Ar^2$ is preferably a group represented by the formula (a-1), (b-1), (c-1), (d-1), (e-1), (f-1), (g-1), (h-1), (p-1), (q-1) or (r-1) wherein Y in the formulae (f-1), (g-1), (h-1), (p-1), (q-1) and (r-1) is preferably S, more preferably a group represented by the formula (g-1), (h-1), (p-1), (q-1) or (r-1) wherein Y in the formulae is preferably S, still more preferably a group represented by the formula (fa-1), (gb-1), (gc-1), (gd-1), (ge-1), (gf-1), (gg-1), (gh-1), (gi-1), (gj-1), (ha-1) or (hb-1).

When n is 2 in the formula (B), $Ar^2$ is preferably a group represented by the formula (a-2), (b-2), (c-2), (d-2), (e-2), (f-2), (g-2), (h-2), (p-2), (q-2) or (r-2) wherein Y in the formulae (f-2), (g-2), (h-2), (p-2), (q-2) and (r-2) is preferably S, more preferably a group represented by the formula (g-2), (h-2), (p-2), (q-2) or (r-2) wherein Y in the formulae is preferably S, still more preferably a group represented by the formula (fa-2), (gb-2), (gc-2), (gd-2), (ge-2), (gf-2), (gg-2), (gh-2), (gi-2), (gj-2), (ha-2) or (hb-2).

The compound represented by the formula (B) is a compound represented by the formula (B-1) or the formula (B-2). Hereinafter, the compound represented by the formula (B-1) is described as compound (B-1) in some cases and the compound represented by the formula (B-2) is described as compound (B-2) in some cases,

$$Ar^2\text{—}X^2 \qquad (B\text{-}1)$$

$$X^2\text{—}Ar^2\text{—}X^2 \qquad (B\text{-}2)$$

wherein, $X^2$ and $Ar^2$ are the same as defined above.

The compound represented by the formula (B-1) includes phenyl bromide, o-tolyl bromide, m-tolyl bromide, p-tolyl bromide, 4-tert-butylphenyl bromide, 2,6-dimethylphenyl bromide, 2,4-dimethylphenyl bromide, 3,5-dimethylphenyl bromide, 2-(2-hydroxyethyl)phenyl bromide, 4-cyclohexylphenyl bromide, 3-bromobenzotrifluoride, 3-bromo-4-chlorobenzotrifluoride, 2-naphthyl bromide, 9-bromoanthracene, 9,10-dibromoanthracene, m-methoxyphenyl bromide, 4-bromobenzaldehyde, methyl 2-bromophenylacetate, methyl 3-bromophenylacetate, methyl 4-bromophenylacetate, methyl 3-bromocinnamate, methyl 5-bromosalicylate, 4-bromobenzamide, 4-bromobenzonitrile, 9-bromophenanthrene, 2-bromofluorene, 5-bromoindanone, 6-bromo-2-naphthol, 2-pyrimidinyl bromide, 2-bromofuran, 3-bromofuran, 2-bromothiophene, 4-bromopyrazole, 2-bromothiazole, 2-methyl-5-bromobenzothiazole, 5-bromouracil, 8-bromoquinoline, 4-bromoisoquinoline, 1-benzyl-5-bromotetrazole, phenyl chloride, o-tolyl chloride, 4-tert-butylphenyl chloride, 3-chlorotoluene, 4-chlorotoluene, 2,6-dimethylphenyl chloride, 3,5-dimethylphenyl chloride, 4-cyclohexylphenyl chloride, 2-chloroacetophenone, 4-chloroacetophenone, 2-chloro-4-fluorotoluene, methyl 2-chlorophenylacetate, methyl 3-chlorophenylacetate, methyl 4-chlorophenylacetate, 3-chlorobenzophenone, 4-chloro-1-naphthol, 4-chloro-N,N-dimethylaniline, 4-chloro-N,N-diphenylaniline, 5-chloro-N,N-dimethylaniline, 5-chloro-2-methoxyaniline, methyl 2-chlorobenzoate, methyl 4-chlorobenzoate, phenyl 2-chlorobenzoate, N-(2-chlorophenyl)acetamide, N-(4-chlorophenyl)acetamide, 2-chlorobenzyl cyanide, 1-naphthyl chloride, 2-naphthyl chloride, 9-chloroanthracene, 2-methoxyphenyl chloride, 3-methoxyphenyl chloride, 4-methoxyphenyl chloride, 3,5-dimethoxy-2-chlorotoluene, 3-chlorobenzonitrile, 2-chloro-3-morpholino-1,4-naphthoquinone, 3-chlorobenzaldehyde, 2-pyridyl chloride, 2-chloro-6-trifluoropyridine, 2-chloro-3-picoline, 1-(3-chlorophenyl)-3-methyl-2-pyrazolin-5-one, 3-chlorothiophene, 2-chloro-3-methylthiophene, 5-chloro-1-methylimidazole, 5-chloro-1-methylbenzotriazole, 5-chloro-1-phenyl-1H-tetrazole, 4-chloro-1-methylindole, 2-chloro-benzimidazole, 8-chloro-5-methoxyquinoline, 2-chlorobenzooxazole, 2-methyl-5-chlorobenzooxazole, 2-chlorobenzothiazole, 2-methyl-5-chlorobenzothiazole, 6-chloro-9-methyl-9H-purine, 2-chloropyrazine, phenyl iodide, o-tolyl iodide, 4-tert-butylphenyl iodide, 2,6-dimethylphenyl iodide, 3,5-dimethylphenyl iodide, 4-iodoacetophenone, ethyl 2-iodobenzoate, 2-naphthyl iodide, 9-iodoanthracene, 3-methoxyphenyl iodide, N-tert-butoxycarbonyl-4-iodophenylalanine methyl ester, 2-methyl-5-iodobenzooxazole, 2-methyl-5-iodobenzothiazole, 2-pyridyl iodide, 2-methyl-5-(p-toluenesulfonyloxy)benzooxazole, phenyltrifluoromethane sulfonate, 4-methylphenyltrifluoromethane sulfonate, 2,6-dimethylphenyltrifluoromethane sulfonate and 2-methyl-5-(trifluoromethanesulfonyloxy)benzothiazole.

The compound represented by the formula (B-2) includes 2,7-dibromo-9,9-dihexyl-9H-fluorene, 2,7-dibromo-9,9-dioctyl-9H-fluorene, 2,7-dibromo-9,9-didodecyl-9H-fluorene, 2,7-dichloro-9,9-dihexyl-9H-fluorene, 2,7-dichloro-9,9-dioctyl-9H-fluorene, 2,7-dichloro-9,9-didodecyl-9H-fluorene, 2-bromo-7-chloro-9,9-dihexyl-9H-fluorene, 2-bromo-7-chloro-9,9-dioctyl-9H-fluorene, 2-bromo-7-chloro-9,9-didodecyl-9H-fluorene, 1,4-dibromobenzene, 1,3-dibromobenzene, 1,4-dibromo-2-ethylbenzene, 1,4-dibromo-2-methoxybenzene, dimethyl-2,5-dibromoterephthalate, 1,4-dibromonaphthalene, 3,5-dibromopyridine, 1,1'-dibromo-4,4'-biphenyl, 2,5-dibromopyridine, 1,4-dibromo-2,5-dihexyloxybenzene, 1-bromo-4-chlorotoluene, 1-bromo-4-chloro-2-propylbenzene, 2,5-dibromo-3-hexylthiophene, 2,5-dibromo-3-octylthiophene, 2,5-dibromo-3-dodecylthiophene, 2,5-dichloro-3-hexylthiophene, 5,5'-dibromo-2,2'-bithiophene, 5,5'-dibromo-3,3'-dihexyl-2,2'-bithiophene, 2,5-dibromothieno[3,2-b]thiophene, 2,5-dibromothieno[2,3-b]thiophene, 4,7-dibromo-2,1,3-benzothiadiazole, 4,7-dibromo-2,1,3-benzoselenadiazole, 4,7-dibromo-5,6-difluoro-2,1,3-benzothiadiazole, 4,7-bis(5-bromo-2-thienyl)-2,1,3-benzothiadiazole, 4,7-bis(5-bromo-4-methyl-2-thienyl)-2,1,3-benzothiadiazole, 4,7-bis(5-bromo-3-methyl-2-thienyl)-2,1,3-benzothiadiazole, 3,7-dibromo-10-(4-n-butylphenyl)-10H-phenothiazine, 3,7-dibromo-10-(4-n-butylphenyl)-10H-phenoxazine, 2,7-dibromo-5,5-didodecyl-5H-dithieno[3,2-b:2',3'-d]pyran, 2,7-dibromo-5,5-bis(3,7-dimethyloctyl)-5H-dithieno[3,2-b:2',3'-d]pyran, 2,6-dibromo-4,4-dioctyl-4H-cyclopenta[2,1-b:3,4-b']bithiophene, 2,6-dibromo-4,4-di(3-ethylhexyl)-4H-cyclopenta[2,1-b:3,4-b']bithiophene, 2,6-dibromo-4,4-dioctyl-4H-silolo[3,2-b:4,5-b']bithiophene, 2,7-dibromo-5,5-dodecylbenzo[2,1-b:3,4-b']dithiophene-4(5H)-one and 2,6-dibromo-4-hexyl-4H-dithieno[3,2-b:2',3'-d]pyrrole, preferably 2,7-dibromo-9,9-didodecyl-9H-fluorene, 1,4-dibromobenzene, 1,3-dibromobenzene-2,5-dibromo-3-hexylthiophene, 2,5-dibromo-3-octylthiophene, 2,5-dibromo-3-dodecylthiophene, 2,5-dibromothieno[3,2-b]thiophene, 2,5-dibromothieno[2,3-b]thiophene, 4,7-dibromo-2,1,3-benzothiadiazole, 4,7-dibromo-5,6-difluoro-2,1,3-benzothiadiazole, 4,7-bis(5-bromo-2-thienyl)-2,1,3-benzothiadiazole, 4,7-bis(5-bromo-4-methyl-2-thienyl)-2,1,3-benzothiadiazole, 4,7-bis(5-bromo-3-methyl-2-thienyl)-2,1,3-benzothiadiazole, 2,7-dibromo-5,5-didodecyl-5H-dithieno[3,2-b:2',3'-d]pyran, 2,7-dibromo-5,5-bis(3,7-dimethyloctyl)-5H-dithieno[3,2-b:2',3'-d]pyran, 2,6-dibromo-4,4-dioctyl-4H-cyclopenta[2,1-b:3,4-b']bithiophene, 2,6-dibromo-4,4-di(3-ethylhexyl)-4H-cyclopenta[2,1-b:3,4-b']bithiophene, 2,6-dibromo-4,4-dioctyl-4H-silolo[3,2-b:4,5-b']bithiophene, 2,7-dibromo-5,5-dodecylbenzo[2,1-b:3,4-b']dithiophene-4(5H)-one and 2,6-dibromo-4-hexyl-4H-dithieno[3,2-b:2',3'-d]pyrrole, more preferably 2,5-dibromo-3-hexylthiophene, 2,5-dibromo-3-octylthiophene, 2,5-dibromo-3-dodecylthiophene, 4,7-dibromo-2,1,3-benzothiadiazole, 4,7-dibromo-5,6-difluoro-2,1,3-benzothiadiazole, 2,7-dibromo-5,5-didodecyl-5H-dithieno[3,2-b:2',3'-d]pyran, 2,7-dibromo-5,5-bis(3,7-dimethyloctyl)-5H-dithieno[3,2-b:2',3'-d]pyran and 2,7-dibromo-5,5-dodecylbenzo[2,1-b:3,4-b']dithiophene-4(5H)-one.

In the process of the present invention, two or more kinds of the compounds represented by the formula (B) may be used in combination.

<Palladium Complex Represented by the Formula (C) and the Formula (C')>

In the process of the present invention, a palladium complex represented by the formula (C) or the formula (C') is used.

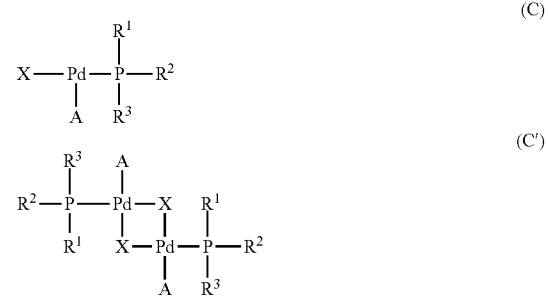

In the crystalline state, the palladium complex may take the form of a palladium complex represented by the formula (C), and the form of a palladium complex having a binuclear structure represented by the formula (C') in which two molecules of the palladium complex represented by the formula (C) are bonded, depending on the kind of $R^1$, $R^2$, $R^3$ or X, recrystallization conditions in producing a palladium complex, and the like.

In the formula (C) and the formula (C'), X is preferably a chlorine atom.

The alkyl group having a number of carbon atoms of 1 to 3 represented by A in the formula (C) and the formula (C') includes a methyl group, an ethyl group, a n-propyl group and an isopropyl group, preferably a methyl group.

In the formula (C) and the formula (C'), $R^1$ is preferably an aryl group having a number of carbon atoms of 6 to 20 and optionally having a substituent or a heteroaryl group having a number of carbon atoms of 4 to 20 and optionally having a substituent.

In the formula (C) and the formula (C'), $R^2$ and $R^3$ each independently represent preferably an alkyl group having a number of carbon atoms of 1 to 6 or a cycloalkyl group having a number of carbon atoms of 5 to 6.

In the formula (C) and the formula (C'), at least two selected from the group consisting of $R^1$, $R^2$ and $R^3$ may be the same, or all of them may be different. It is preferable that at least two selected from the group consisting of $R^1$, $R^2$ and $R^3$ are the same, and it is more preferable that two selected from the group consisting of $R^1$, $R^2$ and $R^3$ are the same.

The alkyl group having a number of carbon atoms of 1 to 20 represented by $R^1$, $R^2$ and $R^3$ in the formula (C) and the formula (C') includes a methyl group, an ethyl group, a n-propyl group, an isopropyl group, a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl group, preferably alkyl groups having a number of carbon atoms of 1 to 6, more preferably a tert-butyl group.

The cycloalkyl group having a number of carbon atoms of 5 to 10 represented by $R^1$, $R^2$ and $R^3$ in the formula (C) and the formula (C') includes a cyclopentyl group, a cyclohexyl group, a cycloheptyl group, a cyclooctyl group, a cyclononyl group and a 1-adamantyl group, preferably a cyclopentyl group or a cyclohexyl group, more preferably a cyclopentyl group.

The aryl group having a number of carbon atoms of 6 to 20 and optionally having a substituent represented by $R^1$ in the formula (C) and the formula (C') includes a phenyl group, a 2-methylphenyl group, a 3-methylphenyl group, a 4-methylphenyl group, a 2,3-dimethylphenyl group, a 2,4-dimethylphenyl group, a 2,5-dimethylphenyl group, a 2,6-dimethylphenyl group, a 3,5-dimethylphenyl group, a 2,4,6-trimethylphenyl group, a 2,3,5,6-tetramethylphenyl group, a 2-ethylphenyl group, a 3,5-diethylphenyl group, a 4-n-propylphenyl group, a 4-isopropylphenyl group, a 4-n-butylphenyl group, a 4-tert-butylphenyl group, a 1-naphthyl group, a 2-naphthyl group, a 2-biphenyl group, a 3-biphenyl group, a 4-biphenyl group, a 2-fluoro-4-biphenyl group, a 2-fluorenyl group, a 9-phenanthrenyl group, a 9-anthracenyl group, a 1-pyrenyl group, a 2-trifluoromethylphenyl group, a 3-trifluoromethylphenyl group, a 4-trifluoromethylphenyl group, a 3,5-bis(trifluoromethyl)phenyl group, a 2-methoxyphenyl group, a 3-methoxyphenyl group, a 4-methoxyphenyl group, a 2,4-dimethoxyphenyl group, a 2,5-dimethoxyphenyl group, a 2,6-dimethoxyphenyl group, a 3,4-dimethoxyphenyl group, a 3,5-dimethoxyphenyl group, a 2-ethoxyphenyl group, a 3-ethoxyphenyl group, a 4-ethoxyphenyl group, a 2-(benzyloxy)phenyl group, a 2-phenoxyphenyl group, a 4-phenoxyphenyl group, a 2,3-methylenedioxyphenyl group, a 3,4-methylenedioxyphenyl group, a 2-fluorophenyl group, a 3-fluorophenyl group, a 4-fluorophenyl group, a 2,4-difluorophenyl group, a 2,5-difluorophenyl group, a 2,6-difluorophenyl group, a 3,4-difluorophenyl group, a 3,5-difluorophenyl group, a 2-formylphenyl group, a 3-formylphenyl group, a 4-formylphenyl group, a 3-formyl-4-methoxyphenyl group, a 2-cyanophenyl group, a 3-cyanophenyl group, a 4-cyanophenyl group, a 2-acetylphenyl group, a 3-acetylphenyl group, a 4-acetylphenyl group, a 4-biphenyl group, a 3-carboxyphenyl group, a 3-aminophenyl group, a 2-(N,N-dimethylamino)phenyl group, a 3-(N,N-dimethylamino)phenyl group, a 4-(N,N-dimethylamino)phenyl group and a 2-(N,N-dimethylaminomethyl)phenyl group.

The heteroaryl group having a number of carbon atoms of 4 to 20 and optionally having a substituent represented by $R^1$ in the formula (C) and the formula (C') includes a 2-thienyl group, a 3-methyl-2-thienyl group, a 4-methyl-2-thienyl group, a 5-methyl-2-thienyl group, a 3,4-dimethyl-2-thienyl group, a 3,5-dimethyl-2-thienyl group, a 4,5-dimethyl-2-thienyl group, a 3-thienyl group, a 2-methyl-3-thienyl group, a 4-methyl-3-thienyl group, a 5-methyl-3-thienyl group, a 2,4-dimethyl-3-thienyl group, a 2,5-dimethyl-3-thienyl group, a 4,5-dimethyl-3-thienyl group, a 2-pyrrolyl group, a 1-methyl-2-pyrrolyl group, a 1-phenyl-2-pyrrolyl group, a 3-pyrrolyl group, a 1-methyl-3-pyrrolyl group, a 1-phenyl-3-pyrrolyl group, a 2-furyl group, a 3-furyl group, a 2-pyridyl group, a 3-methyl-2-pyridyl group, a 4-methyl-2-pyridyl group, a 5-methyl-2-pyridyl group, a 6-methyl-2-pyridyl group, a 3-pyridyl group, a 2-methyl-3-pyridyl group, a 4-methyl-3-pyridyl group, a 5-methyl-3-pyridyl group, a 6-methyl-3-pyridyl group, a 3-pyridazinyl group, a 4-pyridazinyl group, a 2-pyrimidinyl group, a 4-pyrimidinyl group, a 5-pyrimidinyl group, a 2-pyrazinyl group, a 2-triazinyl group, a 2-quinolyl group, a 8-quinolyl group, a 1-isoquinolyl group, a 3-isoquinolyl group, a 2-benzothienyl group, a 7-benzothionyl group, a 2-benzofuryl group, a 7-benzofuryl group, a 2-indolyl group, a 1-methyl-2-indolyl group and a 1-phenylindolyl group.

The palladium complex represented by the formula (C) will be described specifically below, and the palladium complex may be a palladium complex having a binuclear structure represented by the formula (C') in which two molecules of the palladium complex represented by the formula (C) are bonded.

The palladium complex represented by the formula (C) includes a palladium complex in which A is an alkyl group having a number of carbon atoms of 1 to 3, a palladium complex in which A is a methyl group, a palladium complex in which $R^3$ and $R^2$ represent an alkyl group having a number of carbon atoms of 4 to 6, a palladium complex in which $R^3$ and $R^2$ represent a cycloalkyl group having a number of carbon atoms of 5 to 6, a palladium complex in which $R^3$ and $R^2$ represent a tert-butyl group, a palladium complex in which $R^3$ and $R^2$ represent a cyclopentyl group, a palladium complex in which $R^3$ and $R^2$ represent a cyclohexyl group, a palladium complex in which $R^1$ is an aryl group having a number of carbon atoms of 6 to 20 and optionally having a substituent, a palladium complex in which $R^1$, $R^2$ and $R^3$ represent a tert-butyl group, a palladium complex in which A is a methyl group and $R^3$ and $R^2$ represent an alkyl group having a number of carbon atoms of 4 to 6, a palladium complex in which A is a methyl group and $R^3$ and $R^2$ represent a cycloalkyl group having a number of carbon atoms of 5 to 6, a palladium complex in which A is a methyl group and $R^3$ and $R^2$ represent a tert-butyl group, a palladium complex in which A is a methyl group and $R^3$ and $R^2$ represent a cyclopentyl group, a palladium complex in which A is a methyl group and $R^3$ and $R^2$ represent a cyclohexyl group, a palladium complex in which A is a methyl group and $R^1$ is an aryl group having a number of carbon atoms of 6 to 20 and optionally having a substituent, a palladium complex in which A is a methyl group and $R^1$, $R^2$ and $R^3$ represent a tert-butyl group, a palladium complex in which X is a chlorine atom and A is an alkyl group having a number of carbon atoms of 1 to 3, a palladium complex in which X is a chlorine atom and A is a methyl group, a palladium complex in which X is a chlorine atom and $R^3$ and $R^2$ represent an alkyl group having a number of carbon atoms of 4 to 6, a palladium complex in which X is a chlorine atom and $R^3$ and $R^2$ represent a cycloalkyl group having a number of carbon atoms of 5 to 6, a palladium complex in which X is a chlorine atom and $R^3$ and $R^2$ represent a tert-butyl group, a palladium complex in which X is a chlorine atom and $R^3$ and $R^2$ represent a cyclopentyl group, a palladium complex in which X is a chlorine atom and $R^3$ and $R^2$ represent a cyclohexyl group, a palladium complex in which X is a chlorine atom and $R^1$ is an aryl group having a number of carbon atoms of 6 to 20 and optionally having a substituent, a palladium complex in which X is a chlorine atom, A is a methyl group and $R^3$ and $R^2$ represent an alkyl group having a number of carbon atoms of 4 to 6, a palladium complex in which X is a chlorine atom, A is a methyl group and $R^3$ and $R^2$ represent a cycloalkyl group having a number of carbon atoms of 5 to 6, a palladium complex in which X is a chlorine atom, A is a methyl group and $R^3$ and $R^2$ represent a tert-butyl group, a palladium complex in which X is a chlorine atom, A is a methyl group and $R^3$ and $R^2$ represent a cyclopentyl group, a palladium complex in which X is a chlorine atom, A is a methyl group and $R^3$ and $R^2$ represent a cyclohexyl group, a palladium complex in which X is a chlorine atom, A is a methyl group and $R^1$ is an aryl group having a number of carbon atoms of 6 to 20 and optionally having a substituent, and a palladium complex in which X is a chlorine atom, A is a methyl group and $R^1$, $R^2$ and $R^3$ represent a tert-butyl group.

Specific examples of the palladium complex represented by the formula (C) include (tri-(tert-butyl)phosphine)chloromethylpalladium, (di(tert-butyl)(4-fluorophenyl)phosphine)chloromethylpalladium, (di(tert-butyl)(3-fluorophenyl)phosphine)chloromethylpalladium, (di(tert-butyl)(4-methylphenyl)phosphine)chloromethylpalladium, (di(tert-butyl)(3-methylphenyl)phosphine)chloromethylpalladium, (di(tert-butyl)(4-ethylphenyl)phosphine)chloromethylpalladium, (di(tert-butyl)(3-ethylphenyl)phosphine)chloromethylpalladium, ((di(tert-butyl) (4-isopropylphenyl)phosphine)chloromethylpalladium, (di(tert-butyl)(3-isopropylphenyl)phosphine) chloromethylpalladium, (di(tert-butyl) (4-tert-butylphenyl)phosphine)chloromethylpalladium, (di(tert-butyl) (3-tert-butylphenyl)phosphine)chloromethylpalladium, (di(tert-butyl)(4-methoxyphenyl)phosphine)chloromethylpalladium, (di(tert-butyl) (3-methoxyphenyl)phosphine)chloromethylpalladium, (di(tert-butyl)(4-ethoxyphenyl) phosphine) chloromethylpalladium, (di(tert-butyl)(3-ethoxyphenyl)phosphine)chloromethylpalladium, (di(tert-butyl)(4-trifluoromethoxyphenyl)phosphine)chloromethylpalladium, (di(tert-butyl) (3-trifluoromethoxyphenyl)phosphine)chloromethylpalladium, (di(tert-butyl)(4-pentafluoroethoxyphenyl)phosphine)chloromethylpalladium, (di(tert-butyl) (3-pentafluoroethoxyphenyl)phosphine)chloromethylpalladium, (di(tert-butyl) ([1,1'-biphenyl]-4-yl)phosphine)chloromethylpalladium, (di(tert-butyl)([1,1'-biphenyl]-3-yl)phosphine)chloromethylpalladium, (di(tert-butyl) (2-naphthyl)phosphine)chloromethylpalladium, (di(tert-butyl) (3,5-difluorophenyl)phosphine)chloromethylpalladium, (di(tert-butyl) (3,5-dimethylphenyl)phosphine)chloromethylpalladium, (di(tert-butyl) (3,5-diethylphenyl)phosphine)chloromethylpalladium, (di(tert-butyl) (3,5-diisopropylphenyl)phosphine)chloromethylpalladium, (di(tert-butyl) (3,5-di(tert-butyl)phenyl)phosphine) chloromethylpalladium, (di(tert-butyl) (3,5-dimethoxyphenyl)phosphine)chloromethylpalladium, (di(tert-butyl)(3,5-diethoxyphenyl)phosphine) chloromethylpalladium, (di(tert-butyl) (3,5-di(trifluoromethoxy)phenyl)phosphine)chloromethylpalladium, (di(tert-butyl) (3,5-di(trifluoroethoxy)phenyl)phosphine)chloromethylpalladium, (di(tert-butyl) (1,1':3',1''-terphenyl)-5'-yl)phosphine) chloromethylpalladium, (di(tert-butyl)(2-methoxyphenyl) phosphine) chloromethylpalladium, (di(tert-butyl) (3-methoxyphenyl)phosphine) chloromethylpalladium, (di(tert-butyl)(4-methoxyphenyl)phosphine) chloromethylpalladium, (di(tert-butyl) (2,3-dimethoxyphenyl)phosphine) chloromethylpalladium, di(tert-butyl) (2,4-dimethoxyphenyl)phosphine)chloromethylpalladium, di(tert-butyl) (2,5-dimethoxyphenyl)phosphine)chloromethylpalladium, di(tert-butyl) (2,6-dimethoxyphenyl)phosphine)chloromethylpalladium, (tricyclopentylphosphine)chloromethylpalladium, (dicyclopentyl(4-fluorophenyl)phosphine)chloromethylpalladium, (dicyclopentyl(3-fluorophenyl)phosphine) chloromethylpalladium, (dicyclopentyl(4-methylphenyl)phosphine) chloromethylpalladium, (dicyclopentyl(3-methylphenyl) phosphine)chloromethylpalladium, (dicyclopentyl(4-ethylphenyl)phosphine)chloromethylpalladium, (dicyclopentyl(3-ethylphenyl)phosphine)chloromethylpalladium, (dicyclopentyl(4-isopropylphenyl)phosphine)chloromethylpalladium, (dicyclopentyl(3-isopropylphenyl)phosphine) chloromethylpalladium, (dicyclopentyl(4-tert-butylphenyl) phosphine)chloromethylpalladium, (dicyclopentyl(3-tert-butylphenyl)phosphine)chloromethylpalladium, (dicyclopentyl(4-methoxyphenyl)phosphine)chloromethylpalladium, (dicyclopentyl(3-methoxyphenyl)phosphine) chloromethylpalladium, (dicyclopentyl(4-ethoxyphenyl) phosphine)chloromethylpalladium, (dicyclopentyl(3-ethoxyphenyl)phosphine)chloromethylpalladium, (dicyclopentyl(4-trifluoromethoxyphenyl)phosphine)chloromethylpalladium, (dicyclopentyl(3-trifluoromethoxyphenyl)phosphine)chloromethylpalladium, (dicyclopentyl(4-pentafluoroethoxyphenyl)phosphine)chloromethylpalladium, (dicyclopentyl(3-pentafluoroethoxyphenyl) phosphine)chloromethylpalladium, (dicyclopentyl([1,1'-biphenyl]-4-yl)phosphine)chloromethylpalladium, (dicyclopentyl([1,1'-biphenyl]-3-yl)phosphine)chloromethylpalladium, (dicyclopentyl(2-naphthyl)phosphine)chloromethylpalladium, (dicyclopentyl(3,5-difluorophenyl)

phosphine)chloromethylpalladium, (dicyclopentyl(3,5-dimethylphenyl)phosphine)chloromethylpalladium, (dicyclopentyl(3,5-diethylphenyl)phosphine)chloromethylpalladium, (dicyclopentyl(3,5-diisopropylphenyl)phosphine)chloromethylpalladium, (dicyclopentyl(3,5-di(tert-butyl)phenyl)phosphine)chloromethylpalladium, (dicyclopentyl(3,5-dimethoxyphenyl)phosphine)chloromethylpalladium, (dicyclopentyl(3,5-diethoxyphenyl)phosphine)chloromethylpalladium, (dicyclopentyl(3,5-di(trifluoromethoxy)phenyl)phosphine)chloromethylpalladium, (dicyclopentyl(3,5-di(trifluoroethoxy)phenyl)phosphine)chloromethylpalladium (dicyclopentyl(1,1':3',1'-terphenyl)-5'-yl)phosphine)chloromethylpalladium, (dicyclopentyl(2-methoxyphenyl)phosphine)chloromethylpalladium, (dicyclopentyl(3-methoxyphenyl)phosphine)chloromethylpalladium, (dicyclopentyl(4-methoxyphenyl)phosphine)chloromethylpalladium, (dicyclopentyl(2,3-dimethoxyphenyl)phosphine)chloromethylpalladium, (dicyclopentyl(2,4-dimethoxyphenyl)phosphine) chloromethylpalladium, (dicyclopentyl(2,5-dimethoxyphenyl)phosphine)chloromethylpalladium, (dicyclopentyl(2,6-dimethoxyphenyl)phosphine)chloromethylpalladium, (tricyclohexylphosphine)chloromethylpalladium, (dicyclohexyl(4-fluorophenyl)phosphine)chloromethylpalladium, (dicyclohexyl(3-fluorophenyl)phosphine) chloromethylpalladium, (dicyclohexyl(4-methylphenyl)phosphine)chloromethylpalladium, (dicyclohexyl(3-methylphenyl)phosphine)chloromethylpalladium, (dicyclohexyl(4-ethylphenyl)phosphine)chloromethylpalladium, (dicyclohexyl(3-ethylphenyl)phosphine)chloromethylpalladium, (dicyclohexyl(4-isopropylphenyl)phosphine)chloromethylpalladium, (dicyclohexyl(3-isopropylphenyl)phosphine)chloromethylpalladium, (dicyclohexyl(4-tert-butylphenyl)phosphine)chloromethylpalladium, (dicyclohexyl(3-tert-butylphenyl)phosphine)chloromethylpalladium, (dicyclohexyl(4-methoxyphenyl)phosphine)chloromethylpalladium, (dicyclohexyl(3-methoxyphenyl)phosphine)chloromethylpalladium, (dicyclohexyl(4-ethoxyphenyl)phosphine) chloromethylpalladium, (dicyclohexyl(3-ethoxyphenyl)phosphine) chloromethylpalladium, (dicyclohexyl(4-trifluoromethoxyphenyl)phosphine)chloromethylpalladium, (dicyclohexyl(3-trifluoromethoxyphenyl)phosphine)chloromethylpalladium, (dicyclohexyl(4-pentafluoroethoxyphenyl)phosphine)chloromethylpalladium, (dicyclohexyl(3-pentafluoroethoxyphenyl)phosphine)chloromethylpalladium, (dicyclohexyl([1,1'-biphenyl]-4-yl)phosphine)chloromethylpalladium, (dicyclohexyl([1,1'-biphenyl]-3-yl)phosphine)chloromethylpalladium, (dicyclohexyl(2-naphthyl)phosphine)chloromethylpalladium, (dicyclohexyl(3,5-difluorophenyl)phosphine)chloromethylpalladium, (dicyclohexyl(3,5-dimethylphenyl)phosphine)chloromethylpalladium, (dicyclohexyl(3,5-diethylphenyl)phosphine)chloromethylpalladium, (dicyclohexyl(3,5-diisopropylphenyl)phosphine)chloromethylpalladium, (dicyclohexyl(3,5-di(tert-butyl)phenyl)phosphine)chloromethylpalladium, (dicyclohexyl(3,5-dimethoxyphenyl)phosphine)chloromethylpalladium, (dicyclohexyl) (3,5-diethoxyphenyl)phosphine)chloromethylpalladium, (dicyclohexyl)(3,5-di(trifluoromethoxy)phenyl)phosphine)chloromethylpalladium, (dicyclohexyl(3,5-di(trifluoroethoxy)phenyl)phosphine) chloromethylpalladium, (dicyclohexyl(1,1':3',1'-terphenyl)-5'-yl)phosphine)chloromethylpalladium, (dicyclohexyl(2-methoxyphenyl)phosphine)chloromethylpalladium, (dicyclohexyl(3-methoxyphenyl)phosphine)chloromethylpalladium, (dicyclohexyl(4-methoxyphenyl)phosphine) chloromethylpalladium, (dicyclohexyl(2,3-dimethoxyphenyl)phosphine)chloromethylpalladium, (dicyclohexyl(2,4-dimethoxyphenyl)phosphine) chloromethylpalladium, (dicyclohexyl(2,5-dimethoxyphenyl)phosphine)chloromethylpalladium and (dicyclohexyl(2,6-dimethoxyphenyl)phosphine)chloromethylpalladium, preferably (tri-(tert-butyl)phosphine) chloromethylpalladium, (di(tert-butyl) (4-fluorophenyl)phosphine)chloromethylpalladium, (di(tert-butyl) (3-fluorophenyl)phosphine) chloromethylpalladium, (di(tert-butyl)(4-methylphenyl)phosphine)chloromethylpalladium, (di(tert-butyl) (3-methylphenyl)phosphine) chloromethylpalladium, (di(tert-butyl) (4-ethylphenyl)phosphine) chloromethylpalladium, (di(tert-butyl) (3-ethylphenyl)phosphine) chloromethylpalladium, ((di(tert-butyl) (4-isopropylphenyl)phosphine)chloromethylpalladium, (di(tert-butyl) (3-isopropylphenyl)phosphine) chloromethylpalladium, (di(tert-butyl) (4-tert-butylphenyl)phosphine)chloromethylpalladium, (di(tert-butyl) (3-tert-butylphenyl)phosphine) chloromethylpalladium, (di(tert-butyl)(4-methoxyphenyl)phosphine) chloromethylpalladium, (di(tert-butyl) (3-methoxyphenyl)phosphine) chloromethylpalladium, (di(tert-butyl)(4-ethoxyphenyl)phosphine) chloromethylpalladium, (di(tert-butyl) (3-ethoxyphenyl)phosphine) chloromethylpalladium, (di(tert-butyl)(4-trifluoromethoxyphenyl)phosphine)chloromethylpalladium, (di(tert-butyl)(3-trifluoromethoxyphenyl)phosphine)chloromethylpalladium, (di(tert-butyl) (4-pentafluoroethoxyphenyl)phosphine)chloromethylpalladium, (di(tert-butyl) (3-pentafluoroethoxyphenyl)phosphine)chloromethylpalladium, (di(tert-butyl) ([1,1'-biphenyl]-4-yl)phosphine)chloromethylpalladium, (di(tert-butyl) ([1,1'-biphenyl]-3-yl) phosphine) chloromethylpalladium, (di(tert-butyl) (2-naphthyl)phosphine)chloromethylpalladium, (di(tert-butyl)(3,5-difluorophenyl)phosphine) chloromethylpalladium, (di(tert-butyl) (3,5-dimethylphenyl)phosphine)chloromethylpalladium, (di(tert-butyl)(3,5-diethylphenyl)phosphine)chloromethylpalladium, (di(tert-butyl) (3,5-diisopropylphenyl)phosphine)chloromethylpalladium, (di(tert-butyl) (3,5-di(tert-butyl)phenyl)phosphine) chloromethylpalladium, (di(tert-butyl) (3,5-dimethoxyphenyl)phosphine) chloromethylpalladium, (di(tert-butyl)(3,5-diethoxyphenyl)phosphine)chloromethylpalladium, (di(tert-butyl) (3,5-di(trifluoromethoxy)phenyl)phosphine) chloromethylpalladium, (di(tert-butyl) (3,5-di (trifluoroethoxy)phenyl)phosphine)chloromethylpalladium, (di(tert-butyl) (1,1':3',1'''-terphenyl)-5'-yl)phosphine)chloromethylpalladium, (di(tert-butyl)(2-methoxyphenyl)phosphine) chloromethylpalladium, (di(tert-butyl) (3-methoxyphenyl)phosphine) chloromethylpalladium, (di(tert-butyl) (4-methoxyphenyl)phosphine) chloromethylpalladium, (di(tert-butyl) (2,3-dimethoxyphenyl)phosphine) chloromethylpalladium, di(tert-butyl) (2,4-dimethoxyphenyl)phosphine)chloromethylpalladium, di(tert-butyl) (2,5-dimethoxyphenyl)phosphine)chloromethylpalladium and di(tert-butyl) (2,6-dimethoxyphenyl)phosphine)chloromethylpalladium, more preferably (tri-(tert-butyl)phosphine) chloromethylpalladium, (di(tert-butyl)(3,5-difluorophenyl)phosphine) chloromethylpalladium, (di(tert-butyl) (3,5-dimethylphenyl) phosphine) chloromethylpalladium, (di(tert-butyl) (3,5-diethylphenyl)phosphine) chloromethylpalladium, (di(tert-butyl) (3,5-diisopropylphenyl)phosphine) chloromethylpalladium, (di(tert-butyl) (3,5-di(tert-butyl)phenyl)phosphine)chloromethylpalladium, (di(tert-butyl) (3,5-dimethoxyphenyl)phosphine)chloromethylpalladium, (di(tert-butyl) (3,5-diethoxyphenyl)phosphine)chloromethylpalladium, (di(tert-butyl) (3,5-di(trifluoromethoxy)phenyl)phosphine)chloromethylpalladium, (di(tert-butyl) (3,5-di(trifluoroethoxy)phenyl)phosphine)chloromethylpalladium and (di(tert-butyl) (1,1':3',1''-terphenyl)-5'-yl)phosphine)chloromethylpalladium.

In the process of the present invention, two or more kinds of the palladium complex represented by the formula (C) may be used in combination and two or more kinds of the palladium complex represented by the formula (C') may be used in combination.

The palladium complex represented by the formula (C) can be synthesized according to known methods such as Organometallics 2006, 25, 4588-4595.

<Palladium Complex Represented by the Formula (D) and the Formula (D')>

The palladium complex represented by the formula (C) is preferably a palladium complex represented by the formula (D) from the standpoint of stability of the complex. The palladium complex represented by the formula (C') is preferably a palladium complex represented by the formula (D') from the standpoint of stability of the complex. The palladium complexes represented by the formula (D) and the formula (D') may be used as a catalyst for the Suzuki coupling or may be used as a catalyst for the Stille coupling, the Heck coupling, the Hiyama coupling, the Sonogashira coupling, the Kumada coupling and the Buchwald-Hartwig coupling.

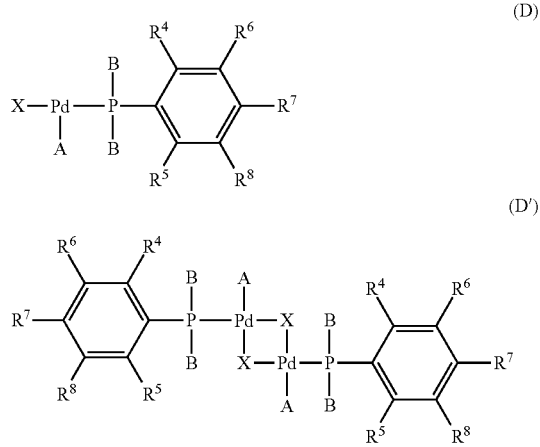

In the formula (D) and the formula (D'), X is preferably a chlorine atom.

The alkyl group having a number of carbon atoms of 1 to 3 represented by A in the formula (D) and the formula (D') includes a methyl group, an ethyl group, a n-propyl group and an isopropyl group, and it is preferably a methyl group from the standpoint of preparation of a catalyst.

In the formula (D) and the formula (D'), B is preferably an alkyl group having a number of carbon atoms of 4 to 20.

The alkyl group having a number of carbon atoms of 4 to 20 represented by B in the formula (D) and the formula (D') includes a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl, preferably alkyl groups having a number of carbon atoms of 4 to 6, more preferably a tert-butyl group.

The cycloalkyl group having a number of carbon atoms of 5 to 10 represented by B in the formula (D) and the formula (D') includes a cyclopentyl group, a cyclohexyl group, a cycloheptyl group, cyclooctyl group and an adamantyl group, preferably cycloalkyl groups having a number of carbon atoms of 5 to 6, more preferably a cyclopentyl group.

The alkoxy group having a number of carbon atoms of 1 to 20 represented by $R^4$ and $R^5$ in the formula (D) and the formula (D') includes a methoxy group, an ethoxy group, a n-propoxy group, an isopropoxy group, a n-butoxy group, a sec-butoxy group, a tert-butoxy group, a n-pentyloxy group, a 2,2-dimethylpropoxy group, a n-hexyloxy group, a n-heptyloxy group, a n-octyloxy group, a n-nonyloxy group, a n-decyloxy group, a n-undecyloxy group, a n-dodecyloxy group, a n-tridecyloxy group, a n-tetradecyloxy group, a n-pentadecyloxy group, a n-hexadecyloxy group, a n-heptadecyloxy group, a n-octadecyloxy group, a n-nonadecyloxy group and a n-icosyloxy group, preferably alkoxy groups having a number of carbon atoms of 1 to 6.

The cycloalkoxy group having a number of carbon atoms of 5 to 10 represented by $R^4$ and $R^5$ in the formula (D) and the formula (D') includes a cyclopentyloxy group and a cyclohexyloxy group.

In the formula (D) and the formula (D'), $R^4$ and $R^5$ represent preferably a hydrogen atom, an alkoxy group having a number of carbon atoms of 1 to 6 or a cycloalkoxy group having a number of carbon atoms of 5 to 6, more preferably a hydrogen atom or an alkoxy group having a number of carbon atoms of 1 to 3, still more preferably a hydrogen atom.

The alkyl group having a number of carbon atoms of 1 to 20 represented by $R^6$, $R^7$ and $R^8$ in the formula (D) and the formula (D') includes a methyl group, an ethyl group, a n-propyl group, an isopropyl group, a n-butyl group, an isobutyl group, a sec-butyl group, a tert-butyl group, a n-pentyl group, a 2,2-dimethylpropyl group, a n-hexyl group, a n-heptyl group, a 2-methylpentyl group, a n-octyl group, a 2-ethylhexyl group, a n-nonyl group, a n-decyl group, a n-undecyl group, a n-dodecyl group, a n-tridecyl group, a n-tetradecyl group, a n-pentadecyl group, a n-hexadecyl group, a n-heptadecyl group, a n-octadecyl group, a n-nonadecyl group and a n-icosyl, preferably alkyl groups having a number of carbon atoms of 1 to 6, more preferably a tert-butyl group.

The cycloalkyl group having a number of carbon atoms of 5 to 10 represented by $R^6$, $R^7$ and $R^8$ in the formula (D) and the formula (D') includes a cyclopentyl group, a cyclohexyl group, a cycloheptyl group, a cyclooctyl group and a 1-adamantyl group, more preferably a cyclopentyl group and a cyclohexyl group.

The aryl group having a number of carbon atoms of 6 to 20 represented by $R^6$, $R^7$ and $R^8$ in the formula (D) and the formula (D') includes a phenyl group, a 4-methylphenyl group, a 2-methylphenyl group, a 1-naphthyl group, a 2-naphthyl group, a 3-phenanthryl group and a 2-anthryl group.

The heteroaryl group having a number of carbon atoms of 4 to 20 represented by $R^6$, $R^7$ and $R^8$ in the formula (D) and the formula (D') includes a 2-thienyl group, a 3-thienyl group, a 2-pyrrolyl group, a 3-pyrrolyl group, a 2-furyl group, a 3-furyl group, a 2-pyridyl group, a 3-pyridyl group, a 3-pyridazinyl group, a 4-pyridazinyl group, a 2-pyrimidinyl group, a 4-pyrimidinyl group, a 5-pyrimidinyl group, a 2-pyrazinyl group, a 2-triazinyl group, a 2-quinolyl group, a 8-quinolyl group, a 1-isoquinolyl group and a 3-isoquinolyl group.

The palladium complex represented by the formula (D) will be described specifically below, and the palladium complex may be a palladium complex having a binuclear structure represented by the formula (D') in which two molecules of the palladium complex represented by the formula (D) are bonded.

The palladium complex represented by the formula (D) includes a palladium complex in which A is an alkyl group having a number of carbon atoms of 1 to 3, a palladium complex in which A is a methyl group, a palladium complex in which B is an alkyl group having a number of carbon atoms of 4 to 6, a palladium complex in which B is a cycloalkyl group having a number of carbon atoms of 5 to 6, a palladium complex in which B is a tert-butyl group, a palladium complex in which B is a cyclopentyl group, a palladium complex in which B is a cyclohexyl group, a palladium complex in which $R^4$ and $R^5$ represent a hydrogen atom, an alkoxy group having a number of carbon atoms of 1 to 6, a palladium complex in which $R^4$ and $R^5$ represent a hydrogen atom, a palladium complex in which $R^4$ and $R^5$ represent an alkoxy group having a number of carbon atoms of 1 to 6, a palladium complex represented by the formula (D) in which $R^6$ and $R^8$ represent a fluorine atom, an alkyl group having a number of carbon atoms of 1 to 6 or an aryl group having a number of carbon atoms of 6 to 20, a palladium complex in which A is a methyl group, B is an alkyl group having a number of carbon atoms of 4 to 6, a palladium complex in which A is a methyl group, B is a cycloalkyl group having a number of carbon atoms of 5 to 6, a palladium complex in which A is a methyl group, B is a tert-butyl group, a palladium complex in which A is a methyl group, B is a cyclopentyl group, a palladium complex in which A is a methyl group, B is a cyclohexyl group, a palladium complex in which X is a chlorine atom, A is a methyl group, B is an alkyl group having a number of carbon atoms of 4 to 6, a palladium complex in which X is a chlorine atom, A is a methyl group, B is a cycloalkyl group having a number of carbon atoms of 5 to 6, a palladium complex in which X is a chlorine atom, A is a methyl group, B is a tert-butyl group, a palladium complex in which X is a chlorine atom, A is a methyl group, B is a cyclopentyl group, a palladium complex in which X is a chlorine atom, A is a methyl group, B is a cyclohexyl group, a palladium complex in which A is a methyl group, B is an alkyl group having a number of carbon atoms of 4 to 6, $R^4$ and $R^5$ represent a hydrogen atom, a palladium complex in which A is a methyl group, B is a cycloalkyl group having a number of carbon atoms of 5 to 6, $R^4$ and $R^5$ represent a hydrogen atom, a palladium complex in which A is a methyl group, B is a tert-butyl group, $R^4$ and $R^5$ represent a hydrogen atom, a palladium complex in which A is a methyl group, B is a cyclopentyl group, $R^4$ and $R^5$ represent a hydrogen atom, a palladium complex in which A is a methyl group, B is a cyclohexyl group, $R^4$ and $R^5$ represent a hydrogen atom, a palladium complex in which X is a chlorine atom, A is a methyl group, B is an alkyl group having a number of carbon atoms of 4 to 6, $R^4$ and $R^5$ represent a hydrogen atom, a palladium complex in which X is a chlorine atom, A is a methyl group, B is a cycloalkyl group having a number of carbon atoms of 5 to 6, $R^4$ and $R^5$ represent a hydrogen atom, a palladium complex in which X is a chlorine atom, A is a methyl group, B is a tert-butyl group, $R^4$ and $R^5$ represent a hydrogen atom, a palladium complex in which X is a chlorine atom, A is a methyl group, B is a cyclopentyl group, $R^4$ and $R^5$ represent a hydrogen atom, a palladium complex in which X is a chlorine atom, A is a methyl group, B is a cyclohexyl group, $R^4$ and $R^5$ represent a hydrogen atom, a palladium complex in which A is a methyl group, B is an alkyl group having a number of carbon atoms of 4 to 6, $R^4$ and $R^5$ represent an alkoxy group having a number of carbon atoms of 1 to 6, a palladium complex in which A is a methyl group, B is a cycloalkyl group having a number of carbon atoms of 5 to 6, $R^4$ and $R^5$ represent an alkoxy group having a number of carbon atoms of 1 to 6, a palladium complex in which A is a methyl group, B is a tert-butyl group, $R^4$ and $R^5$ represent an alkoxy group having a number of carbon atoms of 1 to 6, a palladium complex in which A is a methyl group, B is a cyclopentyl group, $R^4$ and $R^5$ represent an alkoxy group having a number of carbon atoms of 1 to 6, a palladium complex in which A is a methyl group, B is a cyclohexyl group, $R^4$ and $R^5$ represent an alkoxy group having a number of carbon atoms of 1 to 6, a palladium complex in which X is a chlorine atom, A is a methyl group, B is an alkyl group having a number of carbon atoms of 4 to 6, $R^4$ and $R^5$ represent an alkoxy group having a number of carbon atoms of 1 to 6, a palladium complex in which X is a chlorine atom, A is a methyl group, B is a cycloalkyl group having a number of carbon atoms of 5 to 6, $R^4$ and $R^5$ represent an alkoxy group having a number of carbon atoms of 1 to 6, a palladium complex in which X is a chlorine atom, A is a methyl group, B is a tert-butyl group, $R^4$ and $R^5$ represent an alkoxy group having a number of carbon atoms of 1 to 6, a palladium complex in which X is a chlorine atom, A is a methyl group, B is a cyclopentyl group, $R^4$ and $R^5$ represent an alkoxy group having a number of carbon atoms of 1 to 6, a palladium complex in which X is a chlorine atom, A is a methyl group, B is a cyclohexyl group, $R^4$ and R represent an alkoxy group having a number of carbon atoms of 1 to 6, a palladium complex in which A is a methyl group, B is an alkyl group having a number of carbon atoms of 4 to 6, $R^4$ is a hydrogen atom, $R^5$ represent an alkoxy group having a number of carbon atoms of 1 to 6, a palladium complex in which A is a methyl group, B is a cycloalkyl group having a number of carbon atoms of 5 to 6, $R^4$ is a hydrogen atom, $R^5$ is an alkoxy group having a number of carbon atoms of 1 to 6, a palladium complex in which A is a methyl group, B is a tert-butyl group, $R^4$ is a hydrogen atom, $R^5$ is an alkoxy group having a number of carbon atoms of 1 to 6, a palladium complex in which A is a methyl group, B is a cyclopentyl group, $R^4$ is a hydrogen atom, $R^5$ is an alkoxy group having a number of carbon atoms of 1 to 6, a palladium complex in which A is a methyl group, B is a cyclohexyl group, $R^4$ is a hydrogen atom, $R^5$ is an alkoxy group having a number of carbon atoms of 1 to 6, a palladium complex in which X is a chlorine atom, A is a methyl group, B is an alkyl group having a number of carbon atoms of 4 to 6, $R^4$ is a hydrogen atom, $R^5$ is an alkoxy group having a number of carbon atoms of 1 to 6, a palladium complex in which X is a chlorine atom, A is a methyl group, B is a cycloalkyl group having a number of carbon atoms of 5 to 6, $R^4$ is a hydrogen atom, $R^5$ is an alkoxy group having a number of carbon atoms of 1 to 6, a palladium complex in which X is a chlorine atom, A is a methyl group, B is a tert-butyl group, $R^4$ is a hydrogen atom, $R^5$ is an alkoxy group having a number of carbon atoms of 1 to 6, a palladium complex in which X is a chlorine atom, A is a methyl group, B is a cyclopentyl group, $R^4$ is a hydrogen atom, $R^5$ is an alkoxy group having a number of carbon atoms of 1 to 6, a palladium complex in which X is a chlorine atom, A is a methyl group, B is a cyclohexyl group, $R^4$ is a hydrogen atom, $R^5$ is an alkoxy group having a number of carbon atoms of 1 to 6, a palladium complex in which A is a methyl group, B is an alkyl group having a number of carbon atoms of 4 to 6, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is a cycloalkyl group having a number of carbon atoms of 5 to 6, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is a tert-butyl group, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is a cyclopentyl group, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is a cyclohexyl group, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which X is a chlorine atom, A is a methyl group, B is an alkyl group having a number of carbon atoms of 4 to 6, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which X is a chlorine atom, A is a methyl group, B is a cycloalkyl group having a number of carbon atoms of 5 to 6, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which X is a chlorine atom, A is a methyl group, B is a tert-butyl group, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which X is a chlorine atom, A is a methyl group, B is a cyclopentyl group, $R^7$ is a hydrogen atom, $R^6$ and $R^4$ represent a fluorine atom, an alkyl group having a number of carbon atoms of 1 to 6 or an aryl group having a number of carbon atoms of 6 to 20, a palladium complex in which X is a chlorine atom, A is a methyl group, B is a cyclohexyl group, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is an alkyl group having a number of carbon atoms of 4 to 6, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is a cycloalkyl group having a number of carbon atoms of 5 to 6, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is a tert-butyl group, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is a cyclopentyl group, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is a cyclohexyl group, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which X is a chlorine atom, A is a methyl group, B is an alkyl group having a number of carbon atoms of 4 to 6, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which X is a chlorine atom, A is a methyl group, B is a cycloalkyl group having a number of carbon atoms of 5 to 6, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which X is a chlorine atom, A is a methyl group, B is a tert-butyl group, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which X is a chlorine atom, A is a methyl group, B is a cyclopentyl group, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which X is a chlorine atom, A is a methyl group, B is a cyclohexyl group, $R^4$ and $R^5$ represent a hydrogen atom, $R^7$ is a hydrogen atom, $R^6$ and $R^8$ represent a fluorine element, an alkyl group having a number of carbon atoms of 1 to 6 or an aryl group having a number of carbon atoms of 6 to 20, a palladium complex in which A is a methyl group, B is an alkyl group having a number of carbon atoms of 4 to 6, $R^4$ is a hydrogen atom, $R^5$ is an alkoxy group having a number of carbon atoms of 1 to 6, $R^7$ is a hydrogen atom, $R^6$ and $R^8$ represent a fluorine atom, an alkyl group having a number of carbon atoms of 1 to 6 or an aryl group having a number of carbon atoms of 6 to 20, a palladium complex in which A is a methyl group, B is a cycloalkyl group having a number of carbon atoms of 5 to 6, $R^4$ is a hydrogen atom, $R^5$ is an alkoxy group having a number of carbon atoms of 1 to 6, $R^7$ is a hydrogen atom, $R^6$ and $R^8$ represent a fluorine atom, an alkyl group having a number of carbon atoms of 1 to 6 or an aryl group having a number of carbon atoms of 6 to 20, a palladium complex in which A is a methyl group, B is a tert-butyl group, $R^4$ is a hydrogen atom, $R^5$ is an alkoxy group having a number of carbon atoms of 1 to 6, $R^7$ is a hydrogen atom, $R^6$ and $R^8$ represent a fluorine atom, an alkyl group having a number of carbon atoms of 1 to 6 or an aryl group having a number of carbon atoms of 6 to 20, a palladium complex in which A is a methyl group, B is a cyclopentyl group, $R^4$ is a hydrogen atom, $R^5$ is an alkoxy group having a number of carbon atoms of 1 to 6, $R^7$ is a hydrogen atom, $R^6$ and R represent a fluorine atom, an alkyl group having a number of carbon atoms of 1 to 6 or an aryl group having a number of carbon atoms of 6 to 20, a palladium complex in which A is a methyl group, B is a cyclohexyl group, $R^4$ is a hydrogen atom, $R^5$ is an alkoxy group having a number of carbon atoms of 1 to 6, $R^7$ is a hydrogen atom, $R^6$ and R represent a fluorine atom, an alkyl group having a number of carbon atoms of 1 to 6 or an aryl group having a number of carbon atoms of 6 to 20, a palladium complex in which X is a chlorine atom, A is a methyl group, B is an alkyl group having a number of carbon atoms of 4 to 6, $R^4$ is a hydrogen atom, $R^5$ is an alkoxy group having a number of carbon atoms of 1 to 6, $R^7$ is a hydrogen atom, $R^6$ and $R^8$ represent a fluorine atom, an alkyl group having a number of carbon atoms of 1 to 6 or an aryl group having a number of carbon atoms of 6 to 20, a palladium complex in which X is a chlorine atom, A is a methyl group, B is a cycloalkyl group having a number of carbon atoms of 5 to 6, $R^4$ is a hydrogen atom, $R^5$ is an alkoxy group having a number of carbon atoms of 1 to 6, $R^7$ is a hydrogen atom, $R^6$ and $R^8$ represent a fluorine atom, an alkyl group having a number of carbon atoms of 1 to 6 or an aryl group having a number of carbon atoms of 6 to 20, a palladium complex in which X is a chlorine atom, A is a methyl group, B is a tert-butyl group, $R^4$ is a hydrogen atom, $R^5$ is an alkoxy group having a number of carbon atoms of 1 to 6, $R^7$ is a hydrogen atom, $R^6$ and $R^8$ represent a fluorine atom, an alkyl group having a number of carbon atoms of 1 to 6 or an aryl group having a number of carbon atoms of 6 to 20, a palladium complex in which X is a chlorine atom, A is a methyl group, B is a tert-butyl group, $R^4$ is a hydrogen atom, $R^5$ is an alkoxy group having a number of carbon atoms of 1 to 6, $R^6$, $R^7$ and $R^8$ represent a hydrogen atom, a palladium complex in which X is a chlorine atom, A is a methyl group, B is a cyclopentyl group, $R^4$ is a hydrogen atom, $R^5$ is an alkoxy group having a number of carbon atoms of 1 to 6, $R^7$ is a hydrogen atom, $R^6$ and $R^8$ represent a fluorine atom, an alkyl group having a number of carbon atoms of 1 to 6 or an aryl group having a number of carbon atoms of 6 to 20, a palladium complex in which X is a chlorine atom, A is a methyl group, B is a cyclopentyl group, $R^4$ is a hydrogen atom, $R^5$ is an alkoxy group having a number of carbon atoms of 1 to 6, $R^6$, $R^7$ and $R^8$ represent a hydrogen atom, and a palladium complex in which X is a chlorine atom, A is a methyl group, B is a cyclohexyl group, $R^4$ is a hydrogen atom, $R^5$ is an alkoxy group having a number of carbon atoms of 1 to 6, $R^7$ is a hydrogen atom, $R^6$ and $R^8$ represent a fluorine atom, an alkyl group having a number of carbon atoms of 1 to 6 or an aryl group having a number of carbon atoms of 6 to 20.

Specific examples of the palladium complex represented by the formula (D) include (di(tert-butyl) (4-fluorophenyl)phosphine)chloromethylpalladium, (di(tert-butyl)(3-fluorophenyl)phosphine)chloromethylpalladium, (di(tert-butyl) (4-methylphenyl)phosphine)chloromethylpalladium, (di(tert-butyl)(3-methylphenyl)phosphine) chloromethylpalladium, (di(tert-butyl) (4-ethylphenyl)phosphine) chloromethylpalladium, (di(tert-butyl) (3-ethylphenyl)phosphine) chloromethylpalladium, ((di(tert-butyl) (4-isopropylphenyl)phosphine)chloromethylpalladium, (di(tert-butyl) (3-isopropylphenyl)phosphine) chloromethylpalladium, (di(tert-butyl) (4-tert-butylphenyl)phosphine) chloromethylpalladium, (di(tert-butyl) (3-tert-butylphenyl)phosphine) chloromethylpalladium, (di(tert-butyl)(4-methoxyphenyl)phosphine) chloromethylpalladium, (di(tert-butyl) (3-methoxyphenyl) phosphine) chloromethylpalladium, (di(tert-butyl)(4-ethoxyphenyl)phosphine) chloromethylpalladium, (di(tert-butyl) (3-ethoxyphenyl)phosphine) chloromethylpalladium, (di(tert-butyl)(4-trifluoromethoxyphenyl)phosphine)chloromethylpalladium, (di(tert-butyl)(3-trifluoromethoxyphenyl)phosphine)chloromethylpalladium, (di(tert-butyl) (4-pentafluoroethoxyphenyl)phosphine)chloromethylpalladium, (di(tert-butyl)(3-pentafluoroethoxyphenyl) chloromethylpalladium, (di(tert-butyl) ([1,1'-biphenyl]-4-yl)phosphine)chloromethylpalladium, (di(tert-butyl) ([1,1'-biphenyl]-3-yl)phosphine) chloromethylpalladium, (di(tert-butyl) (2-naphthyl)phosphine) chloromethylpalladium, (di(tert-butyl) (3,5-difluorophenyl)phosphine) chloromethylpalladium, (di(tert-butyl) (3,5-dimethylphenyl)phosphine) chloromethylpalladium, (di(tert-butyl)(3,5-diethylphenyl) phosphine)chloromethylpalladium, (di(tert-butyl) (3,5-diisopropylphenyl)phosphine)chloromethylpalladium, (di(tert-butyl) (3,5-di(tert-butyl)phenyl)phosphine) chloromethylpalladium, (di(tert-butyl) (3,5-dimethoxyphenyl)phosphine) chloromethylpalladium, (di(tert-butyl)(3,5-diethoxyphenyl)phosphine)chloromethylpalladium, (di(tert-butyl) (3,5-di(trifluoromethoxy)phenyl)phosphine) chloromethylpalladium, (di(tert-butyl) (3,5-di(trifluoroethoxy)phenyl)phosphine)chloromethylpalladium, (di(tert-butyl) (1,1':3',1''-terphenyl)-5'-yl)phosphine)chloromethylpalladium, (dicyclopentyl)(4-fluorophenyl)phosphine)chloromethylpalladium, (dicyclopentyl)(3-fluorophenyl)phosphine) chloromethylpalladium, (dicyclopentyl)(4-methylphenyl) phosphine)chloromethylpalladium, (dicyclopentyl(3-methylphenyl)phosphine)chloromethylpalladium, (dicyclopentyl) (4-ethylphenyl)phosphine)chloromethylpalladium, (dicyclopentyl(3-ethylphenyl)phosphine)chloromethylpalladium, (dicyclopentyl(4-isopropylphenyl)phosphine)chloromethylpalladium, (dicyclopentyl(3-isopropylphenyl)phosphine)chloromethylpalladium, (dicyclopentyl(4-tert-butylphenyl)phosphine)chloromethylpalladium, (dicyclopentyl(3-tert-butylphenyl)phosphine) chloromethylpalladium, (dicyclopentyl(4-methoxyphenyl)

phosphine)chloromethylpalladium, (dicyclopentyl(3-methoxyphenyl)phosphine)chloromethylpalladium, (dicyclopentyl(4-ethoxyphenyl)phosphine)chloromethylpalladium, (dicyclopentyl(3-ethoxyphenyl)phosphine) chloromethylpalladium, (dicyclopentyl(4-trifluoromethoxyphenyl)phosphine)chloromethylpalladium, (dicyclopentyl (3-trifluoromethoxyphenyl)phosphine) chloromethylpalladium, (dicyclopentyl(4-pentafluoroethoxyphenyl)phosphine)chloromethylpalladium, (dicyclopentyl(3-pentafluoroethoxyphenyl)phosphine)chloromethylpalladium, (dicyclopentyl([1,1'-biphenyl]-4-yl)phosphine)chloromethylpalladium, (dicyclopentyl([1,1'-biphenyl]-3-yl)phosphine) chloromethylpalladium, (dicyclopentyl(2-naphthyl)phosphine)chloromethylpalladium, (dicyclopentyl(3,5-difluorophenyl)phosphine)chloromethylpalladium, (dicyclopentyl (3,5-dimethylphenyl)phosphine)chloromethylpalladium, (dicyclopentyl(3,5-diethylphenyl)phosphine)chloromethylpalladium, (dicyclopentyl(3,5-diisopropylphenyl)phosphine)chloromethylpalladium, (dicyclopentyl(3,5-di(tert-butyl)phenyl)phosphine)chloromethylpalladium, (dicyclopentyl(3,5-dimethoxyphenyl)phosphine)chloromethylpalladium, (dicyclopentyl(3,5-diethoxyphenyl)phosphine)chloromethylpalladium, (dicyclopentyl(3,5-di(trifluoromethoxy)phenyl)phosphine)chloromethylpalladium, (dicyclopentyl(3,5-di(trifluoroethoxy)phenyl)phosphine) chloromethylpalladium, (dicyclopentyl(1,1':3',1'-terphenyl)-5'-yl)phosphine)chloromethylpalladium, (dicyclohexyl(4-fluorophenyl)phosphine)chloromethylpalladium, (dicyclohexyl(3-fluorophenyl)phosphine)chloromethylpalladium, (dicyclohexyl(4-methylphenyl)phosphine)chloromethylpalladium, (dicyclohexyl(3-methylphenyl)phosphine)chloromethylpalladium, (dicyclohexyl(4-ethylphenyl)phosphine)chloromethylpalladium, (dicyclohexyl(3-ethylphenyl)phosphine)chloromethylpalladium, (dicyclohexyl(4-isopropylphenyl)phosphine) chloromethylpalladium, (dicyclohexyl(3-isopropylphenyl)phosphine)chloromethylpalladium, (dicyclohexyl(4-tert-butylphenyl)phosphine)chloromethylpalladium, (dicyclohexyl(3-tert-butylphenyl)phosphine)chloromethylpalladium, (dicyclohexyl(4-methoxyphenyl)phosphine) chloromethylpalladium, dicyclohexyl(3-methoxyphenyl)phosphine)chloromethylpalladium, (dicyclohexyl(4-ethoxyphenyl)phosphine)chloromethylpalladium, (dicyclohexyl(3-ethoxyphenyl)phosphine)chloromethylpalladium, (dicyclohexyl(4-trifluoromethoxyphenyl)phosphine)chloromethylpalladium, (dicyclohexyl(3-trifluoromethoxyphenyl)phosphine)chloromethylpalladium, (dicyclohexyl(4-pentafluoroethoxyphenyl)phosphine)chloromethylpalladium, (dicyclohexyl(3-pentafluoroethoxyphenyl)phosphine)chloromethylpalladium, (dicyclohexyl([1,1'-biphenyl]-4-yl)phosphine)chloromethylpalladium, (dicyclohexyl([1,1'-biphenyl]-3-yl)phosphine)chloromethylpalladium, (dicyclohexyl(2-naphthyl)phosphine)chloromethylpalladium, (dicyclohexyl(3,5-difluorophenyl)phosphine)chloromethylpalladium, (dicyclohexyl(3,5-dimethylphenyl)phosphine)chloromethylpalladium, (dicyclohexyl(3,5-diethylphenyl)phosphine) chloromethylpalladium, (dicyclohexyl(3,5-diisopropylphenyl)phosphine)chloromethylpalladium, (dicyclohexyl(3,5-di(tert-butyl)phenyl)phosphine)chloromethylpalladium, (dicyclohexyl(3,5-dimethoxyphenyl)phosphine)chloromethylpalladium, (dicyclohexyl(3,5-diethoxyphenyl)phosphine)chloromethylpalladium, (dicyclohexyl(3,5-di(trifluoromethoxy)phenyl)phosphine)chloromethylpalladium (dicyclohexyl(3,5-di(trifluoroethoxy)phenyl)phosphine) chloromethylpalladium and (dicyclohexyl(1,1':3',1"-terphenyl)-5'-yl)phosphine)chloromethylpalladium, preferably (di(tert-butyl)(4-fluorophenyl)phosphine)chloromethylpalladium, (di(tert-butyl) (3-fluorophenyl) phosphine) chloromethylpalladium, (di(tert-butyl)(4-methylphenyl)phosphine)chloromethylpalladium, (di(tert-butyl) (3-methylphenyl)phosphine) chloromethylpalladium, (di(tert-butyl)(4-ethylphenyl)phosphine)chloromethylpalladium, (di(tert-butyl) (3-ethylphenyl)phosphine)chloromethylpalladium, ((di(tert-butyl)(4-isopropylphenyl)phosphine) chloromethylpalladium, (di(tert-butyl) (3-isopropylphenyl) phosphine)chloromethylpalladium, (di(tert-butyl) (4-tert-butylphenyl)phosphine)chloromethylpalladium, (di(tert-butyl) (3-tert-butylphenyl)phosphine)chloromethylpalladium, (di(tert-butyl)(4-methoxyphenyl)phosphine) chloromethylpalladium, (di(tert-butyl) (3-methoxyphenyl) phosphine)chloromethylpalladium, (di(tert-butyl)(4-ethoxyphenyl)phosphine)chloromethylpalladium, (di(tert-butyl) (3-ethoxyphenyl)phosphine)chloromethylpalladium, (di(tert-butyl)(4-trifluoromethoxyphenyl)phosphine)chloromethylpalladium, (di(tert-butyl) (3-trifluoromethoxyphenyl) phosphine)chloromethylpalladium, (di(tert-butyl)(4-pentafluoroethoxyphenyl)phosphine)chloromethylpalladium, (di(tert-butyl)(3-pentafluoroethoxyphenyl)phosphine)chloromethylpalladium, (di(tert-butyl) ([1,1'-biphenyl]-4-yl)phosphine)chloromethylpalladium, (di(tert-butyl) ([1,1'-biphenyl]-3-yl)phosphine)chloromethylpalladium, (di(tert-butyl) (2-naphthyl)phosphine)chloromethylpalladium, (di(tert-butyl) (3,5-difluorophenyl)phosphine)chloromethylpalladium, (di(tert-butyl) (3,5-dimethylphenyl)phosphine) chloromethylpalladium, (di(tert-butyl) (3,5-diethylphenyl) phosphine) chloromethylpalladium, (di(tert-butyl) (3,5-diisopropylphenyl)phosphine)chloromethylpalladium, (di(tert-butyl) (3,5-di(tert-butyl)phenyl)phosphine) chloromethylpalladium, (di(tert-butyl) (3,5-dimethoxyphenyl)phosphine)chloromethylpalladium, (di(tert-butyl)(3,5-diethoxyphenyl)phosphine)chloromethylpalladium, (di(tert-butyl) (3,5-di(trifluoromethoxy)phenyl)phosphine)chloromethylpalladium, (di(tert-butyl) (3,5-di(trifluoroethoxy)phenyl)phosphine)chloromethylpalladium and (di(tert-butyl) (1,1':3',1"-terphenyl)-5'-yl) phosphine)chloromethylpalladium, more preferably (di(tert-butyl) (3,5-difluorophenyl)phosphine)chloromethylpalladium, (di(tert-butyl) (3,5-dimethylphenyl)phosphine)chloromethylpalladium, (di(tert-butyl) (3,5-diethylphenyl)phosphine)chloromethylpalladium, (di(tert-butyl) (3,5-diisopropylphenyl)phosphine)chloromethylpalladium, (di(tert-butyl) (3,5-di(tert-butyl)phenyl)phosphine)chloromethylpalladium, (di(tert-butyl)(3,5-dimethoxyphenyl)phosphine)chloromethylpalladium, (di(tert-butyl)(3,5-diethoxyphenyl)phosphine)chloromethylpalladium, (di(tert-butyl) (3,5-di(trifluoromethoxy)phenyl)phosphine)chloromethylpalladium, (di(tert-butyl) (3,5-di(trifluoroethoxy)phenyl)phosphine)chloromethylpalladium and (di(tert-butyl) (1,1':3',1"-terphenyl)-5'-yl) phosphine)chloromethylpalladium.

In the process of the present invention, two or more kinds of the palladium complex represented by the formula (D) may be used in combination and two or more kinds of the palladium complex represented by the formula (D') may be used in combination.

<Process for Producing Palladium Complex Represented by the Formula (D) and the Formula (D')>

The palladium complex represented by the formula (D) and the formula (D') is usually produced by reacting a phosphorus compound represented by the formula (E) with a palladium complex represented by the formula (F) wherein 1,5-cyclooctadiene is coordinated in the palladium complex, in the presence of a solvent,

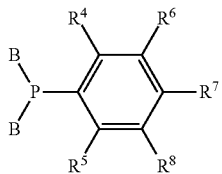
(E)

wherein, B and $R^4$ to $R^8$ are the same as defined above,

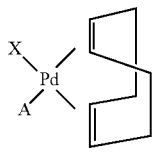
(F)

wherein, A and X are the same as defined above.

The use amount of the phosphorus compound represented by the formula (E) is usually in a range of 1.0 mol to 3.0 mol with respect to 1 mol of the palladium complex in which 1,5-cyclooctadiene is coordinated and which is represented by the formula (F).

The reaction temperature is usually in a range of −30° C. to 80° C.

The reaction time is usually in a range of 1 minute to 24 hours.

The solvent includes chloroform, dichloroethane, diethyl ether, tert-butyl methyl ether and tetrahydrofuran.

The phosphorus compound represented by the formula (E) can be produced, for example, by reacting a phosphonium salt represented by the formula (G) with a base,

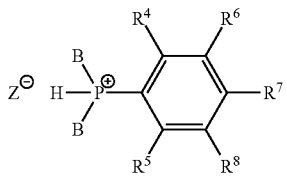
(G)

wherein, B and $R^4$ to $R^8$ are the same as defined above, and $Z^-$ represents an anion.

The anion represented by $Z^-$ includes halogen ions such as $F^-$, $Cl^-$, $Br^-$ and $I^-$, a perchlorate ion, a hydrosulfate ion, a hexafluorophosphate ion and a tetrafluoroborate ion, and a tetrafluoroborate ion is preferable.

The reaction temperature is usually in a range of −30° C. to 80° C.

The reaction time is usually in a range of 1 minute to 6 hours.

The base includes potassium phosphate, sodium phosphate, sodium carbonate, triethylamine and diisopropylamine.

The use amount of the base is usually in a range of 0.5 mol to 3.0 mol with respect to 1 mol of the phosphonium salt represented by the formula (G).

The phosphorus compound represented by the formula (E) may be used after isolation, or may be used without isolation after preparing in the system for producing a palladium complex.

<Organic Solvent>

The process of the present invention is usually carried out in the presence of an organic solvent.

The organic solvent is usually an organic solvent capable of dissolving a compound represented by the formula (A) and a compound represented by the formula (B).

The organic solvent includes ether solvents such as acyclic ether solvents and cyclic ether solvents, aprotic polar solvents, aromatic hydrocarbon solvents, aliphatic hydrocarbon solvents, alcohol solvents, ester solvents and ketone solvents, and preferable are ether solvents, aromatic hydrocarbon solvents, alcohol solvents or ketone solvents.

The acyclic ether solvent includes diethyl ether, diisopropyl ether, ethylene glycol dimethyl ether and diethylene glycol dimethyl ether.

The cyclic ether solvent includes 1,4-dioxane and tetrahydrofuran.

The aromatic hydrocarbon solvent includes benzene, toluene, xylene, mesitylene and tetralin.

The aprotic polar solvent includes N-methylpyrrolidone, N,N-dimethylformamide, N,N-dimethylacetamide, dimethyl sulfoxide and acetonitrile.

The aliphatic hydrocarbon solvent includes hexane, heptane and cyclohexane.

The alcohol solvent includes methanol, ethanol, n-propyl alcohol, isopropyl alcohol, n-butyl alcohol, sec-butyl alcohol and tert-butyl alcohol.

The ester solvent includes ethyl acetate.

The ketone solvent includes acetone and methyl ethyl ketone.

As the organic solvent, toluene, xylene, mesitylene, diethyl ether, diisopropyl ether, ethylene glycol dimethyl ether, diethylene glycol dimethyl ether, 1,4-dioxane, tetrahydrofuran, methanol, ethanol, n-propyl alcohol, isopropyl alcohol, n-butyl alcohol, sec-butyl alcohol, tert-butyl alcohol, ethyl acetate, acetone or methyl ethyl ketone is preferable from the standpoint of solubility of a compound represented by the formula (A) and a compound represented by the formula (B).

In the process of the present invention, two or more organic solvents may be used in combination. Specific examples the combination of two or more organic solvents include a mixed solvent of tetrahydrofuran and toluene, a mixed solvent of methanol and mesitylene and a mixed solvent of acetone and tetralin.

<Base>

The process of the present invention is conducted in the presence of a base. The base may be any one of an inorganic base or an organic base.

The inorganic base includes alkali metal hydroxides, alkaline earth metal hydroxides, alkali metal carboxylates, alkaline earth metal carboxylates, alkali metal carbonates, alkaline earth metal carbonates, alkali metal hydrogencarbonates, alkaline earth metal hydrogencarbonates, alkali metal phosphates and alkaline earth metal phosphates, and alkali metal carbonates and alkali metal phosphates are preferable.

Specific examples of the inorganic base include lithium hydroxide, sodium hydroxide, potassium hydroxide, cesium hydroxide, calcium hydroxide, barium hydroxide, sodium formate, potassium formate, calcium formate, sodium acetate, potassium acetate, sodium carbonate, potassium carbonate, cesium carbonate, calcium carbonate, sodium hydrogen carbonate, potassium hydrogen carbonate, sodium phosphate and potassium phosphate, and sodium carbonate, potassium carbonate, cesium carbonate, sodium phosphate or potassium phosphate is preferable.

The organic base includes alkylammonium hydroxides; alkylammonium carbonates; alkylammonium bicarbonates; alkylammonium borates; 1,5-diazabicyclo[4.3.0]non-5-ene (DBN); 1,8-diazabicyclo[5.4.0]undec-7-ene (DBU); 1,4-diazabicyclo[2.2.2]octane (DABCO); dimethylaminopyridine (DMAP); pyridine; trialkylamines; alkylammonium fluorides such as tetraalkylammonium fluorides, and tetraalkylammonium hydroxides such as tetramethylammonium hydroxide, tetraethylammonium hydroxide, tetra-n-propylammonium hydroxide and the like are preferable.

The use amount of the base is usually in a range of 0.5 equivalents to 20 equivalents, and amounts in a range of 0.5 equivalents to 6 equivalents are preferable. The equivalent represents a ratio of the theoretical substance quantity of a hydrogen ion which the base can neutralize to the total substance quantity of $X^2$ contained in a compound represented by the formula (B).

As the use form of the base, the base may be used as it is, or the base may be used in the form of an aqueous solution.

In the process of the present invention, two or more bases may be used in combination.

<Phase Transfer Catalyst>

When an inorganic base is used as the base in the process of the present invention, a phase transfer catalyst may be used together. The phase transfer catalyst includes tetraalkylammonium halides, tetraalkylammonium hydrosulfates and tetraalkylammonium hydroxides, and tetraalkylammonium halides such as tricaprylmethylammonium chloride (available as Aliquat (registered trademark) 336 from Sigma-Aldrich) are preferable.

The use amount of the phase transfer catalyst is usually in a range of 0.001 equivalent to 1 equivalent, and amounts in a range of 0.01 to 0.5 equivalents are preferable. The equivalent represents a ratio of the substance quantity of the phase transfer catalyst to the total substance quantity of $X^2$ contained in a compound represented by the formula (B).

<Reaction Step>

The process of the present invention comprises a step of reacting a compound represented by the formula (A) with a compound represented by the formula (B) in the presence of a palladium complex represented by the formula (C) or the formula (C'), an organic solvent and a base, and by mixing a compound represented by the formula (A) with a compound represented by the formula (B) in the presence of a palladium complex represented by the formula (C) or the formula (C'), an organic solvent and a base, the compound represented by the formula (A) is reacted with the compound represented by the formula (B), to generate an aromatic compound.

The mixing order of these compounds is not limited, and for example, a compound represented by the formula (A), a compound represented by the formula (B), a palladium complex represented by the formula (C) or the formula (C'), an organic solvent and a base may be mixed simultaneously, or a compound represented by the formula (A), a compound represented by the formula (B), an organic solvent and a base may be mixed and then the resultant mixture, an organic solvent and a palladium complex represented by the formula (C) or the formula (C') may be mixed. A compound represented by the formula (A), a compound represented by the formula (B), a palladium complex represented by the formula (C) or the formula (C') and an organic solvent may be mixed and then the resultant mixture and a base may be mixed.

The use amount of the compound represented by formula (B) is usually in a range of 0.8 mol to 1.2 mol, preferably in a range of 0.9 mol to 1.1 mol with respect to 1 mol of the compound represented by the formula (A).

The use amount of the palladium complex represented by the formula (C) or the formula (C') is usually in a range of 0.0001 mol to 0.8 mol, preferably in a range of 0.001 mol to 0.2 mol with respect to 1 mol of the compound represented by the formula (B).

The reaction temperature of the process of the present invention is usually in a range of −20° C. to 180° C., preferably in a range of −20° C. to 100° C., more preferably in a range of −20° C. to 80° C. When the compound represented by the formula (A) is a compound unstable under the basic condition, for example a boronic acid compound having a hetero ring, the reaction temperature is still more preferably in a range of −20° C. to 60° C.

The reaction time of the process of the present invention is usually in a range of 30 minutes to 96 hours, preferably in a range of 30 minutes to 48 hours.

After completion of the reaction, a reaction mixture containing the desired aromatic compound is obtained. The desired aromatic compound can be isolated from the reaction mixture by purification treatments such as chromatographic fractionation. When the aromatic compound has a repeating unit represented by the formula (F-4), for example, the desired aromatic compound is precipitated by mixing the reaction mixture with a poor solvent, and then the desired aromatic compound can be taken out by usual separation means such as filtration. For removal of impurities such as a palladium complex and a palladium metal from the reaction mixture, the reaction mixture may be washed with an acidic solution such as hydrochloric acid, and then the desired aromatic compound may be taken out.

According to the process of the present invention, an aromatic compound can be produced, irrespective of stability under the basic condition of a compound represented by the formula (A). The reaction temperature of the usual Suzuki coupling is 80° C. or higher, while in the process of the present invention, the reaction progresses even at lower temperatures. Hence, even if the compound represented by the formula (A) is a compound unstable under the basic condition, for example, a boronic acid compound having a hetero ring, the desired aromatic compound can be produced in a high yield, according to the process of the present invention.

In the process of the present invention, if a compound (A-1) and a compound (B-1) are reacted, an aromatic compound represented by the following formula (F-1) is obtained,

$$Ar^1—Ar^2 \qquad (F\text{-}1)$$

wherein, $Ar^1$ and $Ar^2$ are the same as defined above.

In the process of the present invention, if a compound (A-1) and a compound (B-2) are reacted, an aromatic compound represented by the following formula (F-2) is obtained,

$$Ar^1—Ar^2—Ar^1 \qquad (F\text{-}2)$$

wherein, $Ar^1$ and $Ar^2$ are the same as defined above.

In the process of the present invention, if a compound (A-2) and a compound (B-1) are reacted, an aromatic compound represented by the following formula (F-3) is obtained,

$$Ar^2—Ar^1—Ar^2 \qquad (F\text{-}3)$$

wherein, $Ar^1$ and $Ar^2$ are the same as defined above.

In the process of the present invention, if a compound (A-2) and a compound (B-2) are reacted, an aromatic compound having, as a repeating unit, a structural unit represented by the following formula (F-4) is obtained.

$$\{4Ar^1Ar^2\} \quad (F-4)$$

wherein, $Ar^1$ and $Ar^2$ are the same as defined above

EXAMPLES

The present invention will be illustrated further in detail by examples below, but the present invention is not limited to these examples.

The yield of the resultant aromatic compound was calculated from the analysis result by gas chromatography (hereinafter, abbreviated as GC in some cases). The analysis conditions for GC are as described below. When the resultant aromatic compound is an aromatic compound comprising a repeating unit represented by the formula (F-4), the compound was analyzed by gel permeation chromatography (hereinafter, abbreviated as GPC), analysis conditions are as described below, and the polystyrene-equivalent weight-average molecular weight (Mw) and number-average molecular weight (Mn) were calculated from the analysis result and these are used as an index for the yield of the aromatic compound.

<GC Analysis Conditions>
GC measurement apparatus: GC-2010 (manufactured by Shimadzu Corp)
column: DB-1 film thickness 0.25 μm, 300×0.25 mm (manufactured by Agilent Technologies)
temperature of vaporizing chamber: 300° C.
temperature of detector: 300° C.
temperature of column: keeping at 40° C. for 3 minutes, then, raising up to 200° C. at 4.5° C./min, subsequently, raising up to 300° C. at 20° C./min, and then, keeping for 1 minute
injection amount: 1 μL
total flow rate: 13.2 mL/min
column flow rate: 1.70 mL/min
split ratio: 5.0
detection: FID detection <GPC Analysis Condition>
GPC measurement apparatus: CTO-10AC (column oven manufactured by Shimadzu Corp), SPD-10A (detector manufactured by Shimadzu Corp)
column: Shodex KD-806 8.0 mmφ×30 cm (manufactured by SHOWA DENKO K.K.)
temperature of column: 60° C.
mobile phase: ortho-dichlorobenzene
flow rate: 1 mL/min
detection: visible light detection (wavelength 600 nm)

<NMR Measurement Condition>
NMR measurement apparatus: AVANCE600 (manufactured by BRUKER) or JNM-ECA400 (manufactured by JEOL) measurement nucleus: H nucleus, P nucleus Example 1

A nitrogen atmosphere was prepared in a glass reaction vessel, then, 10.6 mmol of di-tert-butyl(3,5-di-(tert-butyl) phenylphosphonium tetrafluoroborate, 20 mL of diethyl ether and 10.6 mmol of triethylamine were added thereto, followed by stirred at room temperature for 5 minutes. A solid was isolated from the resultant suspended liquid by filtration, and the resultant liquid was added into a glass reaction vessel containing 7.5 mmol of chloromethyl(1,5-cyclooctadiene)palladium(II). The resultant mixture was stirred at room temperature for 30 minutes, then, the resultant reaction solution was added dropwise into 94 mL of hexane. The generated solid was isolated by filtration, then, washed three times with 30 mL of hexane. The resultant solid was dried under reduced pressure, to obtain 2.23 g of chloromethyl(di(tert-butyl) (3,5-di(tert-butyl)phenylphosphine)palladium(II) as a white solid.

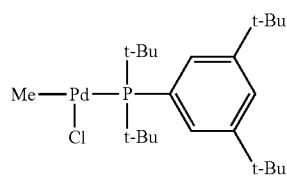

chloromethyl(di(tert-butyl) (3,5-di(tert-butyl)phenylphosphine)palladium(II)

1H-NMR (δ ppm, CDCl$_3$ solvent, TMS standard): 7.6 (dd, 2H), 7.4 (d, 1H), 1.5 (d, 18H), 1.3 (s, 18H), 0.7 (d, 3H)
$^{31}$P-NMR (δ ppm, CDCl$_3$ solvent): 77.4

Example 2

Into a glass reaction vessel equipped with a cooling apparatus were added 0.01 mmol of chloromethyl(tri-tert-butylphosphine)palladium(II), 0.5 mmol of 2-bromo-m-xylene, 0.5 mmol of 2-thiopheneboronic acid, 1.0 mmol of potassium phosphate, 4.5 mL of methanol, 0.5 mL of water, and 0.07 mmol of n-octylbenzene as an internal standard. The resultant mixture was stirred at 0° C. for 3 hours. Two hundred microliters of the resultant reaction mixture was diluted with 5 mL of tetrahydrofuran, then, GC analysis was conducted to find a yield of the desired 2-(2',6'-dimethylphenyl)-thiophene of 94%.

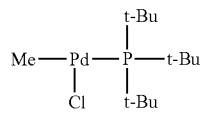

chloromethyl(tri-tert-butylphosphine)palladium(II)

Example 3

2-(2',6'-dimethylphenyl)-thiophene was obtained in the same manner as in Example 2, except that sodium carbonate was used instead of potassium phosphate in Example 2. Its yield was 91%.

Comparative Example 1

2-(2',6'-dimethylphenyl)-thiophene was obtained in the same manner as in Example 2, except that [2-(amino-κN)(1,1'-biphenyl)-2-yl-κC]chloro[tri-(tert-butyl)phosphine] palladium(II) was used instead of chloromethyl(tri-tert-butylphosphine)palladium(II) in Example 2. Its yield was 12%.

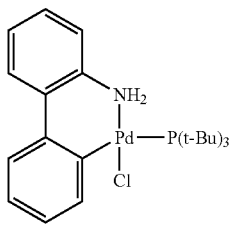

[2-(amino-κN) (1,1'-biphenyl)-2-yl-κC]chloro[tri-(tert-butyl)phosphine]palladium(II)

Comparative Example 2

2-(2',6'-dimethylphenyl)-thiophene was obtained in the same manner as in Example 2, except that [2-(amino-κN)(1,1'-biphenyl)-2-yl-κC]chloro[tri-(tert-butyl)phosphine]palladium(II) was used instead of chloromethyl(tri-tert-butylphosphine)palladium(II) in Example 2 and sodium carbonate was used instead of potassium phosphate in Example 2. Its yield was 75%.

Example 4

Into a glass reaction vessel equipped with a cooling apparatus were added 0.0025 mmol of chloromethyl(di(tert-butyl)) (3,5-di(tert-butyl)phenylphosphine)palladium(II) obtained in Example 1, 0.5 mmol of 2-bromo-m-xylene, 0.5 mmol of 2-thiopheneboronic acid, 1.0 mmol of potassium phosphate, 4.5 mL of tetrahydrofuran, 0.5 mL of water, and 0.07 mmol of n-octylbenzene as an internal standard. The resultant mixture was stirred at 45° C. for 3 hours. Two hundred microliters of the resultant reaction mixture was diluted with 5 mL of tetrahydrofuran, then, GC analysis was conducted to find a yield of the desired 2-(2',6'-dimethylphenyl)-thiophene of 90%.

Example 5

A nitrogen atmosphere was prepared in a glass reaction vessel equipped with a cooling apparatus, then, 3.0 mmol of 4,7-dibromo-5,6-difluoro-2,1,3-benzothiadiazole, 3.0 mmol of 2,2'-(5,5-bis(3,7-dimethyloctyl)-5H-dithieno[3,2-b:2',3'-d]pyran-2,7-diyl)bis(5-methyl-1,3,2-dioxaborinane-5-methanol), 9 μmol of chloromethyl(tri-tert-butylphosphine)palladium(II), 90 mL of water, 70 mL of tetrahydrofuran and 30 mL of mesitylene were added thereto. The resultant mixture was heated at 45° C. while stirring. To the resultant mixture was added 10 mL of a 3M potassium phosphate aqueous solution. The resultant mixture was heated at 45° C. while stirring and reacted for 4 hours, to obtain a reaction mixture containing an aromatic compound comprising a repeating structural unit represented by the following formula. The resultant aromatic reaction mixture was dissolved in 1-chloronaphthalene, then, the molecular weight was analyzed by GPC, to find a molecular weight (Mw) of $3.6 \times 10^4$.

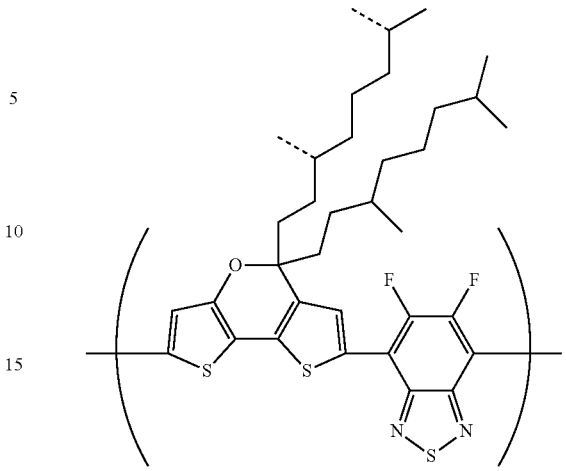

Comparative Example 3

The same procedure as in Example 5 was carried out, except that [2-(amino-κN)(1,1'-biphenyl)-2-yl-KC]chloro[tri-(tert-butyl)phosphine]palladium(II) was used instead of chloromethyl(tri-tert-butylphosphine)palladium(II) in Example 5. The molecular weight (Mw) of the resultant aromatic compound was $2.6 \times 10^4$.

Example 6

Into a glass reaction vessel equipped with a cooling apparatus were added 0.0025 mmol of chloromethyl(tri-tert-butylphosphine)palladium(II), 0.5 mmol of bromobenzene, 0.5 mmol of m-tolylboronic acid, 1.0 mmol of potassium phosphate, 4.5 mL of methanol, 0.5 mL of water, and 0.07 mmol of n-nonylbenzene as an internal standard. The resultant mixture was stirred at 60° C. for 3 hours. Two hundred microliters of the resultant reaction mixture was diluted with 5 mL of tetrahydrofuran, and GC analysis was conducted to find a yield of the desired 3-methylbiphenyl of 100%.

Example 7

Into a glass reaction vessel equipped with a cooling apparatus were added 0.0025 mmol of chloromethyl(di(tert-butyl) (3,5-di(tert-butyl)phenylphosphine)palladium(II)palladium(II), 0.5 mmol of 2-bromo-m-xylene, 0.5 mmol of 2-thiopheneboronic acid, 1.0 mmol of potassium phosphate, 4.5 mL of methanol, 0.5 mL of water, and 0.07 mmol of n-octylbenzene as an internal standard. The resultant mixture was stirred at 25° C. for 3 hours. Two hundred microliters of the resultant reaction mixture was diluted with 5 mL of tetrahydrofuran, then, GC analysis was conducted to find a yield of the desired 2-(2',6'-dimethylphenyl)-thiophene of 95%.

Example 8

A nitrogen atmosphere was prepared in a glass reaction vessel equipped with a dropping funnel, then, 0.18 g of 2-bromoanisole and 4 mL of tetrahydrofuran were added thereto. The resultant solution was cooled down to −70° C., then, 0.6 mL of n-butyllithium (1.63M/hexane solution) was added dropwise. The resultant mixture was stirred at −70° C. for 1 hour, then, a solution prepared by dissolving 0.20 g of chlorodicyclopentylphosphine in 4 mL of tetrahydrofuran was added dropwise. The resultant mixture was stirred at room temperature for 3 hours, then, 5 mL of a NH$_4$Cl aqueous solution (2M) was added, and extracted with 20 mL of hexane twice. The organic layers obtained in respective extractions were mixed, and the mixture was concentrated, to obtain a mixture containing viscous liquid dicyclopentyl(2-methoxyphenyl)phosphine.

A nitrogen atmosphere was prepared in a glass reaction vessel, then, the mixture containing dicyclopentyl(2-methoxyphenyl)phosphine obtained above, 0.20 g of chloromethyl(1,5-cyclooctadiene)palladium(II) and 0.5 mL of tetrahydrofuran were added thereto. The resultant mixture was stirred at room temperature for 5 minutes, then, the resultant reaction solution was added dropwise into 9 mL of hexane. The generated solid was isolated by filtration, and washed three times with 3 mL of hexane. The resultant solid was dried under reduced pressure, to obtain 0.24 g of chloromethyl(dicyclopentyl(2-methoxyphenyl)phosphine)palladium(II) as a gray solid.

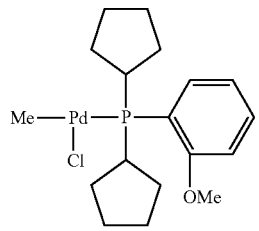

chloromethyl(dicyclopentyl(2-methoxyphenyl)phosphine)palladium(II)

1H-NMR (δ ppm, CDCl$_3$ solvent, TMS standard, 50° C.): 7.6 (t, 1H), 7.4 (t, 1H), 7.04 (t, 1H), 6.98 (s, 1H), 4.1 (s, 3H), 2.6 (d, 2H), 2.1 (m, 2H), 1.9 (s, 2H), 1.8-1.5 (m, 12H), 0.9 (s, 3H)

$^{31}$P-NMR (δ ppm, CDCl$_3$ solvent): 46.8, 35.3

Example 9

A nitrogen atmosphere was prepared in a glass reaction vessel equipped with a dropping funnel, and then, 0.52 g of 2-bromoanisole and 50 mL of tetrahydrofuran were added thereto. The resultant solution was cooled down to −70° C., and then, 1.7 mL of n-butyllithium (1.63M/hexane solution) was added dropwise. The resultant mixture was stirred at −70° C. for 1 hour, and then, a solution prepared by dissolving 0.50 g of ditert-butylchlorophosphine in 17 mL of tetrahydrofuran was added dropwise. The resultant mixture was stirred at room temperature for 3 hours, and then, the resultant reaction mixture was concentrated, to obtain a mixture containing di(tert-butyl)(2-methoxyphenyl)phosphine.

A nitrogen atmosphere was prepared in a glass vessel, and then, the mixture containing di(tert-butyl)(2-methoxyphenyl)phosphine obtained above and 20 mL of diethyl ether were added and mixed. The resultant mixture was filtrated through Celite, to obtain a liquid. Into another glass reaction vessel was added the liquid obtained above. A nitrogen atmosphere was prepared in the vessel, and then, 0.49 g of tetrafluoroboric acid diethyl ether complex was added thereto, and the resultant mixture was stirred vigorously for 30 minutes. The deposited solid was isolated by filtration, then, washed three times with 10 mL of diethyl ether. The resultant solid was dried under reduced pressured at room temperature for 3 hours, to obtain di(tert-butyl)(2-methoxyphenyl)phosphonium tetrafluoroborate as a white solid.

A nitrogen atmosphere was prepared in a glass reaction vessel, and then, 0.8 g of di(tert-butyl)(2-methoxyphenyl)phosphonium tetrafluoroborate obtained above, 2 mL of diethyl ether and 0.7 mL of triethylamine were added thereto and these were stirred at room temperature for 5 minutes. A solid was isolated from the resultant suspended liquid by filtration, and the resultant liquid was added into a glass reaction vessel containing 0.35 g of chloromethyl(1,5-cyclooctadiene)palladium(II). The resultant mixture was stirred at room temperature for 30 minutes, and then, the resultant reaction solution was added dropwise into 17 mL of hexane. The generated solid was isolated by filtration, then, washed three times with 3 mL of hexane. The resultant solid was dried under reduced pressure, to obtain 0.27 g of chloromethyl(di(tert-butyl) ((2-methoxyphenyl)phosphine)palladium(II) as a white solid.

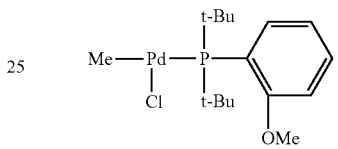

chloromethyl(di(tert-butyl)((2-methoxyphenyl)phosphine)palladium(II)

1H-NMR (δ ppm, CDCl$_3$ solvent, TMS standard): 7.8 (t, 1H), 7.5 (t, 1H), 7.2 (t, 1H), 7.1 (m, 1H), 4.4 (s, 3H), 1.4 (d, 18H), 1.4 (d, 3H)

$^{31}$P-NMR (δ ppm, CDCl$_3$ solvent): 59.8

Example 10

Into a glass reaction vessel equipped with a cooling apparatus were added 0.0025 mmol of chloromethyl(dicyclopentyl(2-methoxyphenyl)phosphine)palladium(II) obtained in Example 8, 0.5 mmol of 2-bromo-m-xylene, 0.5 mmol of 2-thiopheneboronic acid, 1.0 mmol of potassium phosphate, 4.5 mL of tetrahydrofuran, 0.5 mL of water, and 0.07 mmol of n-octylbenzene as an internal standard. The resultant mixture was stirred at 65° C. for 3 hours. Two hundred microliters of the resultant reaction mixture was diluted with 5 mL of tetrahydrofuran, and GC analysis was conducted to find a yield of the desired 2-(2',6'-dimethylphenyl)-thiophene of 92%.

Example 11

2-(2',6'-dimethylphenyl)-thiophene was obtained in the same manner as in Example 10, except that chloromethyl(di(tert-butyl) ((2-methoxyphenyl)phosphine)palladium(II) obtained in Example 9 was used instead of chloromethyl(dicyclopentyl(2-methoxyphenyl)phosphine)palladium(II) in Example 10. Its yield was 92%.

| | palladium complex | base | yield |
|---|---|---|---|
| Example 2 | chloromethyl(tri-tert-butylphosphine)palladium(II) | potassium phosphate | 94% |

-continued

| | palladium complex | base | yield |
|---|---|---|---|
| Example 3 | chloromethyl(tri-tert-butylphosphine)palladium(II) | sodium carbonate | 91% |
| Example 4 | chloromethyl(di(tert-butyl)(3,5-di(tert-butyl)phenylphosphine)palladium(II) | potassium phosphate | 90% |
| Example 7 | chloromethyl(di(tert-butyl)(3,5-di(tert-butyl)phenylphosphine)palladium(II) | potassium phosphate | 95% |
| Example 10 | chloromethyl(dicyclopentyl(2-methoxyphenyl)phosphine)palladium(II) | potassium phosphate | 92% |
| Example 11 | chloromethyl(di(tert-butyl)((2-methoxyphenyl)phosphine)palladium(II) | potassium phosphate | 92% |
| Comparative Example 1 | [2-(amino-κN)(1,1'-biphenyl)-2-yl-κC]chloro[tri-(tert-butyl)phosphine]palladium(II) | potassium phosphate | 12% |
| Comparative Example 2 | [2-(amino-κN)(1,1'-biphenyl)-2-yl-κC]chloro[tri-(tert-butyl)phosphine]palladium(II) | sodium carbonate | 75% |

| | palladium complex | molecular weight (Mw) |
|---|---|---|
| Example 5 | chloromethyl(tri-tert-butylphosphine)palladium(II) | $3.6 \times 10^4$ |
| Comparative Example 3 | [2-(amino-κN)(1,1'-biphenyl)-2-yl-κC]chloro[tri-(tert-butyl)phosphine]palladium(II) | $2.6 \times 10^4$ |

INDUSTRIAL APPLICABILITY

According to the present invention, the process for producing the aromatic compound giving high yield and a catalyst used in the process can be provided.

The invention claimed is:

1. A palladium complex represented by the formula (D) or the formula (D'):

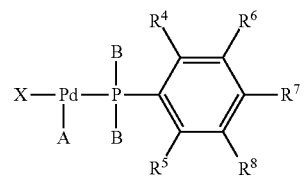

(D)

wherein,
X represents a chlorine atom, a bromine atom or an iodine atom,
A represents an alkyl group having 1 to 3 carbon atoms,
B represents an alkyl group having 4 to 20 carbon atoms or a cycloalkyl group having 5 to 10 carbon atoms,
$R^4$ and $R^5$ each represent a hydrogen atom,
$R^7$ represents a hydrogen atom and $R^6$ and $R^8$ each represent a t-butyl group;

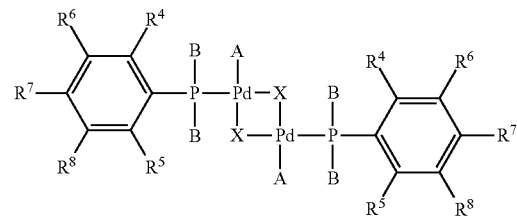

(D')

wherein the plurality of X, A, B and $R^4$ to $R^8$ may be the same or different at each occurrence.

2. The palladium complex according to claim 1, wherein A is a methyl group.

3. The palladium complex according to claim 1, wherein B is an alkyl group having 4 to 20 carbon atoms.

4. The palladium complex according to claim 3, wherein B is an alkyl group having 4 to 6 carbon atoms.

5. The palladium complex according to claim 4, wherein B is a tert-butyl group.

* * * * *